(12) United States Patent
Suzuki et al.

(10) Patent No.: US 9,310,385 B2
(45) Date of Patent: Apr. 12, 2016

(54) PLATELET MEASUREMENT REAGENT, PLATELET MEASUREMENT REAGENT KIT, AND PLATELET MEASUREMENT METHOD

(71) Applicant: SYSMEX CORPORATION, Kobe-shi, Hyogo (JP)

(72) Inventors: Yuhgi Suzuki, Kobe (JP); Keiko Moriyama, Kobe (JP); Yusuke Mori, Kobe (JP); Hiroki Takeshita, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 6 days.

(21) Appl. No.: 14/590,551

(22) Filed: Jan. 6, 2015

(65) Prior Publication Data

US 2015/0185210 A1    Jul. 2, 2015

Related U.S. Application Data

(62) Division of application No. 12/918,240, filed as application No. PCT/JP2009/052685 on Feb. 17, 2009, now Pat. No. 9,081,021.

(30) Foreign Application Priority Data

| Feb. 18, 2008 | (JP) | ................................ | 2008-036013 |
| Mar. 26, 2008 | (JP) | ................................ | 2008-079785 |
| Sep. 26, 2008 | (JP) | ................................ | 2008-247484 |

(51) Int. Cl.
*G01N 33/80* (2006.01)
*G01N 33/52* (2006.01)

(52) U.S. Cl.
CPC ................ *G01N 33/80* (2013.01); *G01N 33/52* (2013.01)

(58) Field of Classification Search
CPC ....................................................... G01N 33/80
See application file for complete search history.

(56) References Cited

U.S. PATENT DOCUMENTS

| 4,336,029 | A  | 6/1982 | Natale |
| 5,891,731 | A  | 4/1999 | Akai et al. |
| 6,114,173 | A  | 9/2000 | Zelmanovic et al. |
| 6,664,110 | B1 | 12/2003 | Tsuji et al. |
| 2002/0034825 | A1 | 3/2002 | Schweigart |
| 2003/0219850 | A1 | 11/2003 | Tsuji et al. |
| 2008/0102526 | A1 | 5/2008 | Mori et al. |

FOREIGN PATENT DOCUMENTS

| EP | 1 136 563 A2 | 9/2001 |
| EP | 1 918 709 A1 | 5/2008 |
| JP | H03-182562 A | 8/1991 |
| JP | 2003-329668 A | 11/2003 |

(Continued)

OTHER PUBLICATIONS

Wainwright et al (Methylene Blue—a Therapeutic Dye for All Seasons?, Journal of Chemotherapy, vol. 14, Issue 5, Jan. 1, 2002, pp. 431-443).*

(Continued)

*Primary Examiner* — Benjamin Packard
(74) *Attorney, Agent, or Firm* — Sughrue Mion, PLLC

(57) ABSTRACT

A reagent for measuring platelets comprising Nile Blue hydrogensulfate, or Nile Blue and an acid, a reagent kit for measuring platelets comprising the reagent for measuring platelets, and a method for measuring platelets using the reagent or reagent kit.

20 Claims, 22 Drawing Sheets

(56) References Cited

FOREIGN PATENT DOCUMENTS

| | | |
|---|---|---|
| JP | 2008-111717 A | 5/2008 |
| JP | 2008-111718 A | 5/2008 |

OTHER PUBLICATIONS

Morgenstern E, et al; "Lipoide als zytochemisches Substrat der Bindungsorte basischer Vitalfarbstroffe in Blut-, Epithel- und Tumorzellen = Lipids as a cytochemical substrate for the binding of basic dyes in blood-, epithel- and tumor cells" Histochemie, Springer, Berlin, DE, vol. 10, No. 4, Jan. 1, 1967, pp. 309-320.

Ostle A G et al; "Nile Blue A As a Fluorescent Stain for Poly-Beta Hydroxy Butyrate", Applied and Environmental Microbiology, vol. 44, No. 1, 1982, pp. 238-241.

Spiekermann Patricia et al; "Sensitive, viable-colony staining method using Nile red for direct screening of bacteria that accumulate polyhydroxyalkanoic acids and other lipid storage compounds", Archives of Microbiology, vol. 171, No. 2, Jan. 1999 (199-01), pp. 73-80.

European Patent Office, Communication pursuant to Article 94(3) EPC issued Oct. 26, 2012 for corresponding Application No. 09 711 933.3-2404.

Safavi et al.: "CCD camera full range pH sensor array" Talanta. 71 (2007) 498-501.

"Merck Millipore catalogue entry No. 115946" Retrieved from the internet: http://www.merckmillipore.com/germany/chemicals/nilblau-hydroge nsulfat-c-i-51180/MDA__CHEM-115946/p_zyOb.s1LZbOAAAEWZuEfVhTI [retrieved on Oct. 22, 2012].

Safavi, et al., "Wide range pH measurements using a single H+ -selective chromoionophore and a time-based flow method", Talanta, Elsevier, Amsterdam, NL, vol. 68, No. 5, Feb. 28, 2006, pp. 1469-1473.

Taylor, et al., "Femtosecond vibrational relaxation of large organic molecules", Chemical Physics Letters, Elsevier BV, NL, vol. 103, No. 5, Jan. 13, 1984, pp. 430-435.

Safavi et al. (Talanta 68 (2006) 1469-1473).

Davis et al., Anal Chem, vol. 38, No. 3 (1966) pp. 451-461.

* cited by examiner

Sample Analyzer

<Measurement unit>  <Data process unit>

PLATELET MEASUREMENT REAGENT, PLATELET MEASUREMENT REAGENT KIT, AND PLATELET MEASUREMENT METHOD

CROSS-REFERENCE TO RELATED APPLICATIONS

This application is a divisional of U.S. patent application Ser. No. 12/918,240, filed on Aug. 18, 2010, which is a National Phase of International Patent Application No. PCT/JP2009/052685, filed on Feb. 17, 2009, which claims priority from Japanese Patent Application Nos. 2008-036013, filed on Feb. 18, 2008, 2008-079785, filed on Mar. 26, 2008, and 2008-247484, filed on Sep. 26, 2008, in the Japanese Patent Office. The disclosures of which are incorporated herein in their entirety by reference.

TECHNICAL FIELD

The present invention relates to a reagent for measuring platelets, a reagent kit for measuring platelets and a method for measuring platelets using the same. More specifically, the present invention relates to the reagent for measuring platelets comprising Nile Blue, particularly Nile Blue hydrogensulfate.

BACKGROUND ART

Methods have been known in which blood cells, i.e. leukocytes, reticulocytes, erythrocytes and the like are rapidly measured by using a principle of flow cytometry.

As one of such measurement methods, for example, U.S. Pat. No. 6,114,173 discloses a method for counting and detecting reticulocytes, erythrocytes and platelets in whole blood samples as well as a reagent composition used for the method. Specifically, reticulocytes are stained with a reagent mixture containing a cationic dye, particularly Oxazine 750, and their scattered light signal and light absorbance signal are measured using flow cytometry. Then, erythrocytes and reticulocytes in blood samples are differentiated by the difference in absorbance signals, and the group of erythrocytes and reticulocytes and platelets are differentiated by the difference in scattered light signals, so as to determine total numbers of each species.

SUMMARY OF INVENTION

Technical Problem

It has been known that fragmented red cells, lipids and the like occurring in blood are similar in size as platelets, so that they affect measurements as contaminants. Especially, samples containing few platelets for which blood transfusion may be required are more significantly affected by these contaminants upon measurements. Such problem may occur in the method disclosed in U.S. Pat. No. 6,114,173. However, U.S. Pat. No. 6,114,173 does not describe that platelets are measured by preventing any effect by the contaminants.

In addition, dyes which can stain platelets may be degraded in a solution with time. Measurements of platelets by flow cytometry are carried out by detecting scattered light and fluorescence obtained by applying light to the cells stained with the dye in samples. However, when a dye solution is used in which the amount of the dye contained for platelet staining has been decreased, accurate scattered light or fluorescence can not be obtained, and accurate measurement results can not be obtained.

The present invention has been achieved in view of the above circumstances, and is intended to provide a reagent and reagent kit for measuring platelets that makes it possible to measure platelets with higher accuracy by preventing the effect of contaminants which may be contained in samples and prevent the detection of platelets and that have high storage stability. The present invention is also intended to provide a method for measuring platelets that makes it possible to measure platelets with higher accuracy.

Means for Solving the Problems

Therefore, the present invention provides a reagent for measuring platelets comprising, as a dye for staining platelets, Nile Blue having hydrogensulfate ion as a counter ion.

The present invention also provides a reagent kit for measuring platelets comprising:
a first reagent comprising, as a dye for staining platelets, Nile Blue having hydrogensulfate ion as a counter ion, and
a second reagent comprising a buffering agent.

Further, the present invention provides a method for measuring platelets comprising the steps of:
mixing a first reagent comprising, as a dye for staining platelets, Nile Blue having hydrogensulfate ion as a counter ion and a sample with or without adding a second reagent comprising a buffering agent to prepare a measurement sample;
applying light to cells in the obtained measurement sample to detect scattered light and fluorescence emitted from the cells; and
detecting platelets contained in the measurement sample based on the detected scattered light and fluorescence.

In another aspect, the present invention provides a reagent for measuring platelets comprising, as a dye for staining platelets, Nile Blue having an inorganic acid ion as a counter ion and an acid.

Further, the present invention provides a reagent kit for measuring platelets comprising:
a first reagent comprising, as a dye for staining platelets, Nile Blue having an inorganic acid ion as a counter ion and an acid, and
a second reagent comprising a buffering agent.

Further, the present invention provides a method for measuring platelets comprising the steps of:
mixing a reagent for measuring platelets comprising Nile Blue and an acid and a sample with or without adding a second reagent comprising a buffering agent to prepare a measurement sample;
applying light to cells in the obtained measurement sample to detect scattered light and fluorescence emitted from the cells; and
detecting platelets contained in the measurement sample based on the detected scattered light and fluorescence.

As used herein, "Nile Blue" denotes dyes consisting of the compound which is represented by, for example, the following formula (II):

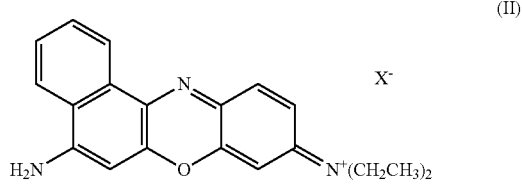

(II)

wherein X is an anion;
and is in the form of a salt with the counter ion represented by X. In the present specification, the dyes represented by the formula (II) in which the counter ion represented by X is not specifically limited are called merely "Nile Blue", and the dyes represented by the formula (II) in which the counter ion is specifically defined are called "Nile Blue XXX (XXX denotes a salt with a particular ion)". For example, the dye having sulfuric ion ($\frac{1}{2}$ $SO_4^{2-}$) as a counter ion is called "Nile Blue sulfate" and the dye having hydrogensulfate ion ($HSO_4^-$) as a counter ion is called "Nile Blue hydrogensulfate".

DESCRIPTION OF THE REFERENCE NUMERALS

Figure 1A:
FIGS. 1A-1B show containers which can contain the reagent kit for measuring platelets of the present invention.

A First container
B Second container
1 Sample analyzer
2 Measurement unit
3 Data process unit
4 Controlling section
5 Detecting section
6 Sample preparing section
7 Interface
8 Controlling section
9 Data analyzing section
10 Display section
11 Operating section
12 Interface
51 Flow cell
52 Laser light source
53 Light application lenses
54 and 57 Photodiodes
54a Beam stopper
54b Amplifier
55 Side condensing lens
56 Dichroic mirror
57 Photodiode
57a and 58b Amplifiers
58 Photomultiplier
58a Optical filter

BEST MODE FOR CARRYING OUT THE INVENTION

Reagent for Measuring Platelets

The present inventors have found that platelets can be clearly distinguished from contaminants in blood such as blood cell components other than platelets or lipid particles by using Nile Blue as a dye for staining platelets in methods for measuring platelets by flow cytometry.

Further, the present inventors have conducted extensive studies for the conditions for measuring platelets using Nile Blue and found that the reagents for measuring platelets have superior storage stability when (1) it contains Nile Blue hydrogensulfate; or (2) it contains Nile Blue and an acid, so as to complete the present invention.

In the above formula (II), the anion (counter ion) of X includes an inorganic acid ion such as sulfuric ion ($\frac{1}{2}$ $SO_4^{2-}$), chloride ion ($Cl^-$), hydrogensulfate ion ($HSO_4^-$), perchloric ion ($ClO_4^-$).

The above Nile Blues are commercially available and are purchased from, for example, Sigma Aldrich, Tokyo Chemical Industry Co., Ltd., Nacalai Tesque, Inc., Wako Pure Chemical Industries, Ltd., Kishida Chemical Co., Ltd. and the like.

Specifically, Nile Blue hydrogensulfate can be purchased from Wako Pure Chemical Industries, Ltd. and Kishida Chemical Co., Ltd.

Nile Blue contained in the reagent for measuring platelets of the present invention (e.g. Nile Blue hydrogensulfate) is preferably contained in a dye reagent in a concentration range so as to obtain the concentration of 0.05 to 5.0 ppm, more preferably 0.1 to 0.6 ppm, further preferably 0.2 to 0.5 ppm when the reagent for measuring platelets is mixed with a sample. For example, when the reagent for measuring platelets is mixed with a sample to the dilution rate of 1/50, the concentration of Nile Blue in the reagent for measuring platelets is preferably 2.5 to 250 ppm.

Platelets are more clearly distinguished from blood cell components other than platelets or contaminants, when Nile Blue is present within the above concentration range.

In the aspect in which the reagent for measuring platelets of the present invention comprises Nile Blue and an acid, the acid may be either of an organic acid or inorganic acid, with the preference of an inorganic acid. The inorganic acid includes oxo-acids such as sulfuric acid, phosphoric acid, perchloric acid, and hydroacids such as hydrochloric acid, hydrofluoric acid, hydroiodic acid, hydrobromic acid, hydrocyanic acid, hydroisocyanic acid, hydrogen sulfide, hydrogen azide.

In the above aspect of the reagent for measuring platelets of the present invention, the acid is contained in the reagent for measuring platelets at the concentration which is equal or lower than the molar concentration of Nile Blue in the reagent for measuring platelets. Specifically, the ratio of molar concentrations of Nile Blue and the acid in the reagent for measuring platelets is preferably 10:1 to 1:1. When the acid is hydrochloric acid, the ratio of molar concentrations of Nile Blue and hydrochloric acid is preferably 3:1 to 1:1. When the acid is sulfuric acid, the ratio of molar concentrations of Nile Blue and sulfuric acid is preferably 4:1 to 1:1. By using the acid at the above concentrations, the reduction of the effective dye component concentration of Nile Blue in the reagent for measuring platelets with time can be effectively prevented, so that the storage stability of the reagent for measuring platelets can be improved.

In the above aspect of the reagent for measuring platelets of the present invention, any combination of Nile Blue and the acid can be used. The more preferred combinations are:
(A) Nile Blue sulfate and an oxo-acid or hydroacid;
(B) Nile Blue chloride and sulfuric acid; and
(C) Nile Blue hydrogensulfate and an oxo-acid or hydroacid.

In another aspect of the reagent for measuring platelets of the present invention, when Nile Blue is Nile Blue hydrogensulfate, the reagent for measuring platelets does not need to contain an acid. When Nile Blue is Nile Blue hydrogensulfate, reduction in the effective dye component concentration of Nile Blue in the reagent for measuring platelets with time can be effectively prevented without an acid, so that the storage stability of the reagent for measuring platelets can be improved.

The following two hypotheses may be given as to why the reagents for measuring platelets of the present invention in the above two aspects have improved storage stability.

(1) It is considered that Nile Blue has high stability when it is in the form of the hydrogensulfate salt.

When an acid is added to Nile Blue sulfate, a proton ($H^+$) which is generated by the dissociation of the acid binds to $SO_4^{2-}$ of Nile Blue sulfate to form $HSO_4^-$, so that $HSO_4^-$ and Nile Blue are in balance of 1:1 and stabilized.

When Nile Blue is a salt other than the above, sulfuric acid may be added, so that $HSO_4^-$ generated from sulfuric acid can stabilize Nile Blue.

Thus, the reagent for measuring platelets of the present invention may be the one comprising Nile Blue and optionally an acid so as to hydrogensulfate ion exists in the reagent.

(2) Nile Blue contains three nitrogen atoms in their diethylamino group, amino group and phenoxazine structure. Among these nitrogen atoms, nitrogen atoms other than the one which forms the salt with the counter anion represented by X in the above formula form an acid addition salt, so that the stability of nitrogen atoms and the solubility of the dye are improved and the stability of the reagent for measuring platelets is improved.

Namely, Nile Blue hydrogensulfate may generate a proton ($H^+$) and sulfuric ion ($SO_4^{2-}$) due to the dissociation of hydrogensulfate ion ($HSO_4^-$). This proton can bind to any of nitrogen atoms of Nile Blue to produce a protic nitrogen atom. It is considered that this protic nitrogen atom forms an intermolecular salt via sulfuric acid, and hence the solubility and stability of the dye can be improved.

When an acid is added to Nile Blue other than the hydrogensulfate salt, it is considered that a proton and an anion generated by the dissociation of the acid contribute to the formation of intermolecular salts of Nile Blue, so that the solubility and stability of the dye can be improved.

Thus, the reagent for measuring platelets of the present invention may be the one comprising Nile Blue and optionally an acid so as to Nile Blue can form an intermolecular salt.

The reagent for measuring platelets of the present invention preferably comprises a water-soluble organic solvent. The water-soluble organic solvent is not specifically limited so long as it can dissolve the above Nile Blue and includes protic solvents such as ethylene glycol, diethylene glycol, poly(ethylene glycol).

The reagent for measuring platelets of the present invention can be prepared by dissolving the above Nile Blue and optionally the acid into the water-soluble organic solvent at the above desired concentration.

<Reagent Kit for Measuring Platelets>

The above reagent for measuring platelets can be combined with a reagent comprising a buffering agent for diluting the reagent for measuring platelets comprising the dye to form a reagent kit.

Thus, the present invention also provides a reagent kit for measuring platelets comprising:
a first reagent comprising Nile Blue hydrogensulfate, or Nile Blue and an acid (hereinafter also referred to as "the dye reagent"); and
a second reagent comprising a buffering agent (hereinafter also referred to as "the dilution reagent").

The details for the first reagent are the same as those described above for the reagent for measuring platelets.

The buffering agent contained in the second reagent may not be specifically limited so long as it can keep pH of the second reagent within a desired range, and can be carboxylates, phosphates, Good Buffers, taurine, triethanolamine depending on the desired pH. The buffering agent is preferably contained in the dilution reagent so as to obtain the pH range of the dilution reagent of 6.0 to 11.0, more preferably 7.0 to 10.0, and further preferably 8.0 to 9.5. When pH of the dilution reagent is 6.0 or above, erythrocytes become resistant to lysing and the contaminants fragmented red cells can be decreased upon the mixture of the dilution reagent and a sample. When pH is 11.0 or below, non-specific staining of fragmented red cells can be reduced.

Thus, the second reagent is preferably a buffer having pH of 6.0 to 11.0.

The dilution reagent may comprise, in addition to the buffering agent, other components such as an osmoticum, a staining accelerating agent for accelerating the staining of platelets by Nile Blue.

The osmoticum may be any compound so long as it can keep the osmotic pressure of the dilution reagent within an appropriate range, and includes alkaline metal salts of an organic acid such as propionic acid, saccharides such as glucose, mannose. Alkaline metal halides such as NaCl and alkaline earth metal halides may also be used. One or more osmoticums can be used.

The osmoticum is preferably contained in the dilution reagent so as to adjust the osmotic pressure of the dilution reagent to 150 to 600 mOsm/kg, and more preferably 200 to 300 mOsm/kg. By adjusting the osmotic pressure within the above range, the osmotic pressure of the mixture of the reagents in the reagent kit and a sample may be closer to the physiological osmotic pressure, so that hemolysis due to hypotonicity can be prevented, increase of fragmented red cells can be suppressed and the measurement of platelets can be more accurate. When the osmotic pressure of the dilution reagent can be adjusted within the above range by using the above buffering agent, the osmoticum may not be required.

The staining accelerating agent may be any compound that can increase the permeability of Nile Blue into platelets, and includes surfactants, particularly preferably cationic surfactants.

The preferable cationic surfactant is the one represented by the following formula (I):

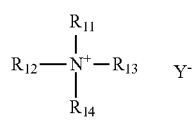

(I)

wherein $R_{11}$ is an alkyl group having 8 to 12 carbon atoms; $R_{12}$, $R_{13}$ and $R_{14}$ are the same or different from each other and are an alkyl group having 1 to 6 carbon atoms; and Y is an anion.

In the above formula (I), the alkyl group having 8 to 12 carbon atoms of $R_{11}$ may be linear or branched and include, for example, octyl, decyl, lauryl, cetyl, myristyl and the like groups.

The alkyl group having 1 to 6 carbon atoms of $R_{12}$, $R_{13}$ and $R_{14}$ may be linear or branched and include, for example, methyl, ethyl, propyl, butyl, isobutyl, sec-butyl, tert-butyl, pentyl, hexyl and the like groups. Among these, methyl and ethyl groups are preferable.

The anion of Y is preferably a bromine or chlorine ion.

The preferable cationic surfactants of the formula (I) include decyltrimethylammonium bromide (DTAB), octyltrimethylammonium bromide (OTAB), lauryltrimethylammonium chloride (LTAC), cetyltrimethylammonium chloride (CTAC), myristyltrimethylammonium bromide (MTAB) and the like. One or more cationic surfactants may be used.

The cationic surfactant is preferably contained in the dilution reagent at the concentration of 50 to 20,000 ppm. The particularly preferable concentration may depend on the type of the cationic surfactants and is preferably 500 to 3,000 ppm when DTAB is used and 100 to 500 ppm when LTAC is used. When the dilution reagent contains the cationic surfactant at such concentrations, hemolysis can be prevented and the staining of platelets can be accelerated upon mixing of the reagents in the reagent kit for measuring platelets and a sample.

The dilution reagent may comprise, in addition to the above components, a preservative such as sodium 2-pyridylthio-1-oxide, β-phenethyl alcohol.

The buffering agent which is contained in the dilution reagent and other components which may optionally be contained in the dilution reagent may be mixed with the dye reagent beforehand. However, because Nile Blue contained in the dye reagent may be degraded with water or an alkaline component, the reagent kit separately comprising the dye reagent and dilution reagent is preferable in view of the storage stability.

Figure 1B:
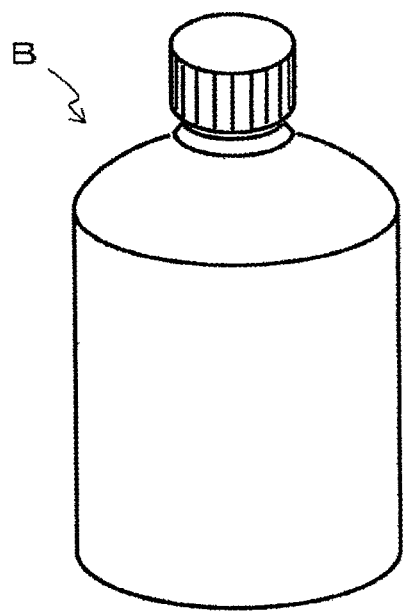

The reagent kit for measuring platelets according to the present embodiment may be contained in a first container A for containing the dye reagent and a second container B for containing the dilution reagent as shown in FIGS. 1A-1B. When the dye reagent and dilution reagent are contained in separate containers, the degradation of Nile Blue contained in the dye reagent can be prevented due to water or an alkaline component contained in the dilution reagent, so that the reagent kit for measuring platelets having a superior storage stability can be provided.

<Method for Measuring Platelets>

The reagent or reagent kit for measuring platelets is mixed with a sample which may contain platelets, thereby staining the platelets.

Thus, the present invention further provides a method for measuring platelets by using the reagent or reagent kit for measuring platelets.

The method for measuring of the present invention comprises the steps of:

mixing a first reagent comprising Nile Blue hydrogensulfate, or Nile Blue and the acid with a sample to prepare a measurement sample;

applying light to cells in the obtained measurement sample to detect scattered light and fluorescence emitted from the cells; and detecting platelets contained in the measurement sample based on the detected scattered light and fluorescence.

In the step of mixing the first reagent and a sample in the above method, a second reagent comprising the buffering agent may be further mixed or not mixed. It is preferable that the second reagent is further mixed.

The details for the first and second reagents are the same as those described above for the reagent kit for measuring platelets.

The sample includes blood (whole blood, platelet rich plasma (PRP) etc.) and bone marrow fluid obtained from organisms, particularly from mammals including human. The sample may be blood or bone marrow fluid diluted with an appropriate solution such as buffer.

The first reagent and the sample are preferably mixed so as to obtain the concentration of Nile Blue in the measurement sample of 0.05 to 5.0 ppm, preferably 0.1 to 0.6 ppm, and further preferably 0.2 to 0.5 ppm.

The first reagent may be diluted with the second reagent in order to achieve the above concentration of Nile Blue in the measurement sample after mixing with the sample.

When the second reagent is used, the first and second reagents and the sample are preferably mixed in the volume ratio of (first reagent+second reagent):sample=100:1 to 1000:1.

When the second reagent is used, the volume ratio between the first and second reagents is preferably 1:10 to 1:100, and more preferably 1:20 to 1:75.

When the second reagent is added in the step of mixing, the mixing order of the first reagent, second reagent and sample is not specifically limited.

The step of mixing can be carried out at a temperature of approximately 25 to 50° C., more preferably approximately 35 to 45° C. The time for mixing is preferably 10 seconds to 5 minutes, more preferably 10 seconds to 2 minutes, and further preferably 10 seconds to 60 seconds.

In the method for measuring of the present invention, light is applied to the cells in the measurement sample thus obtained and scattered light and fluorescence emitted from the cells are detected.

An apparatus for applying light is preferably a flow cytometer. In the flow cytometer, the measurement sample is introduced into a flow cell of the flow cytometer and light is applied to the cells in the measurement sample passing through the flow cell.

The light source of the flow cytometer is not specifically limited and can be any light source suitable for excitation of Nile Blue (e.g. around 600 to 680 nm). The light source includes, for example, red semiconductor laser and He—Ne laser. The semiconductor laser is suitable because it is cheaper than gas laser.

Scattered light emitted from the cells applied with light in the flow cytometer may be either of forward scattered light (light-receiving angle of approximately 0 to 20 degrees) or side scattered light (light-receiving angle of approximately 90 degrees). The forward scattered light may be either of low angle forward scattered light (light-receiving angle of approximately 1 to 5 degrees) or high angle forward scattered light (light-receiving angle of approximately 6 to 20 degrees).

The fluorescence emitted from the cells applied with light in the flow cytometer can be detected by selecting an appropriate light-receiving wave length for Nile Blue (approximately 630 to 680 nm).

Based on the scattered light and fluorescence obtained as above, a scattergram is prepared, so as to detect platelets by distinguishing platelets from contaminants such as blood cell components other than platelets, lipid particles. The thus detected platelets can also be counted. The detection and/or counting of platelets is preferably carried out by using an appropriate analyzing software.

Measurements of platelets using a sample analyzer equipped with a flow cytometer are now described with referring to the attached Figures.

Figure 2:
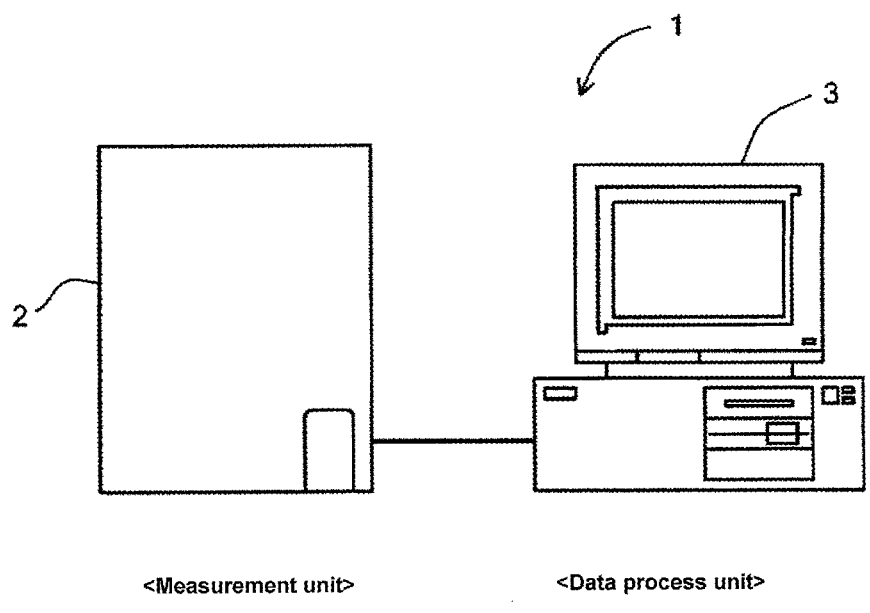
FIG. 2 is a front view of the schematic constitution of a sample analyzer.

FIG. 2 is a front view of the schematic constitution of the sample analyzer. The sample analyzer 1 is an apparatus used for hematological tests, for example, and is mainly composed of a measurement unit 2 and a data process unit 3. In the measurement unit 2, certain components contained in a blood sample are measured, and the data process unit 3 receives the measurement data to carry out an analytical processing.

Figure 3:
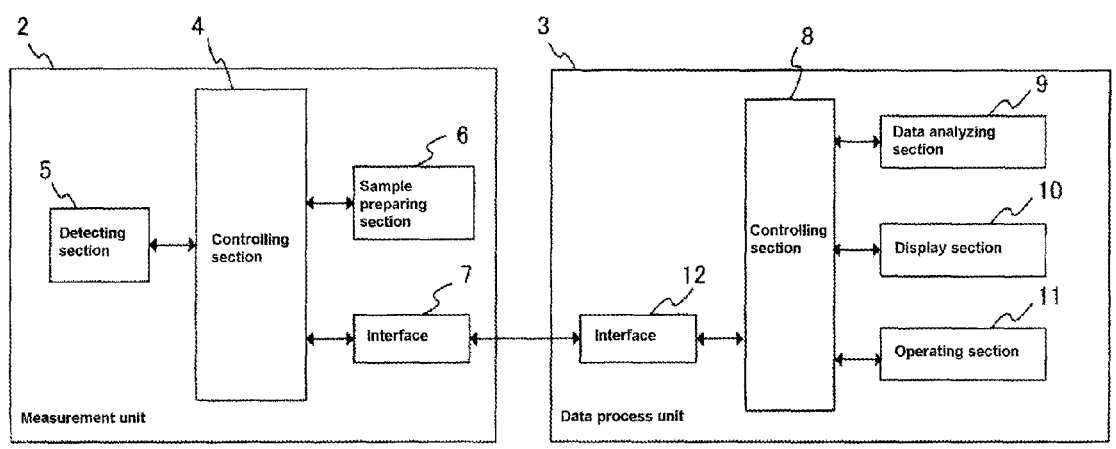
FIG. 3 is a block diagram showing the schematic constitution of the sample analyzer.

FIG. 3 is a block diagram showing the schematic constitution of the sample analyzer 1. As shown in FIG. 3, the measurement unit 2 comprises a controlling section 4 for controlling the action of respective sections; a detecting section 5 equipped with a flow cytometer for detecting particles to be analyzed in the sample; a sample preparing section 6 for preparing a measurement sample and providing the prepared measurement sample to the detecting section 5; and an interface 7 for transmitting data with the data process unit 3. The data process unit 3 comprises a controlling section 8 for controlling the action of respective sections; a data analyzing section 9 for analyzing the detected data received from the measurement unit 2; a display section 10 which displays the analysis results from the data analyzing section 9 as scattergrams; an operating section 11 which accepts operations by an operator; and an interface 12 for transmitting data with the measurement unit 2.

Figure 4:
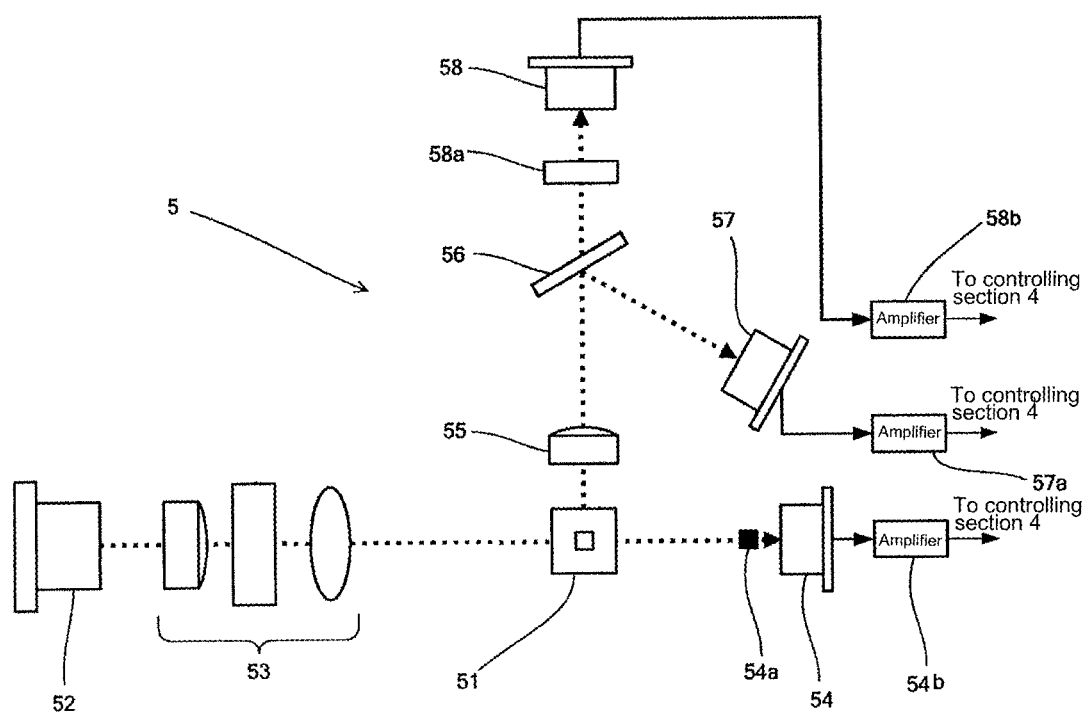
FIG. 4 is a schematic plan view showing the constitution of a detecting section.
Figure 5A:
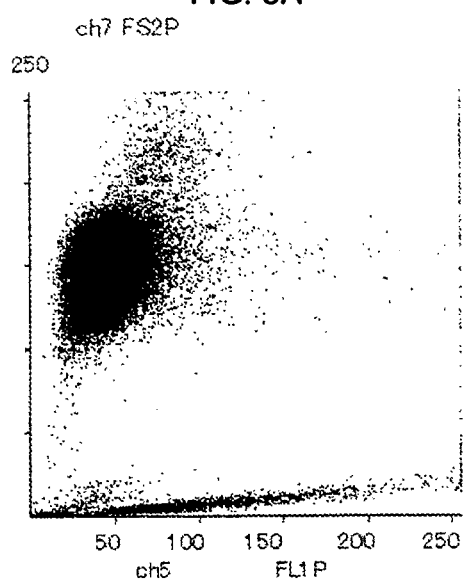
FIGS. 5A-5B show scattergrams obtained by the platelet measurement using the reagent for measuring platelets of Experimental Example 9.
Figure 5B:
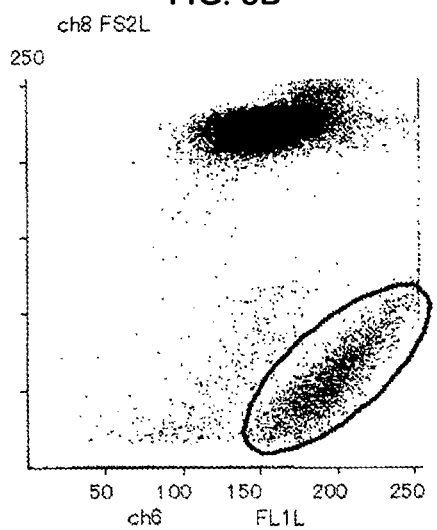
Figure 6A:
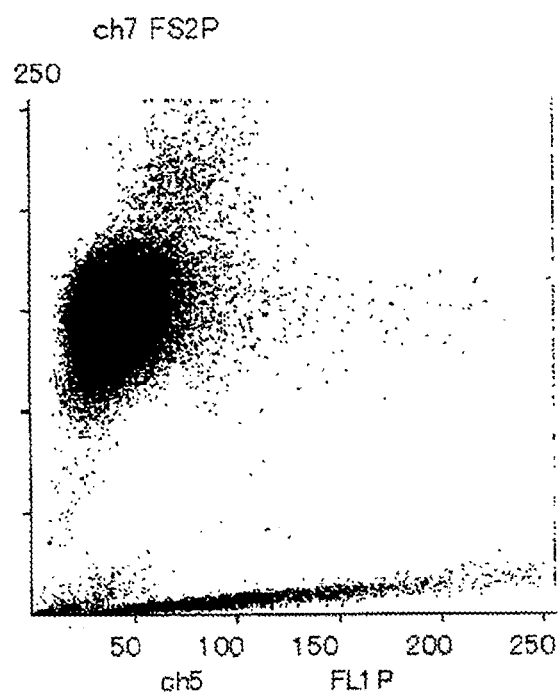
FIGS. 6A-6B show scattergrams obtained by the platelet measurement using the reagent for measuring platelets of Experimental Example 10.
Figure 6B:
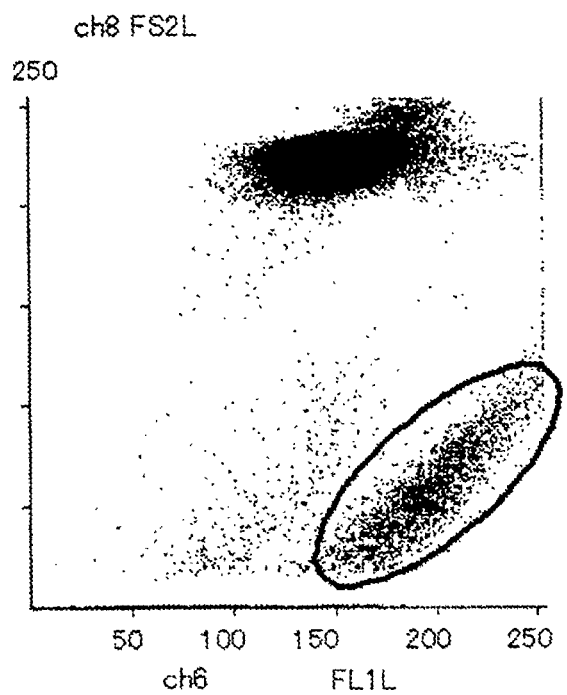
Figure 7A:
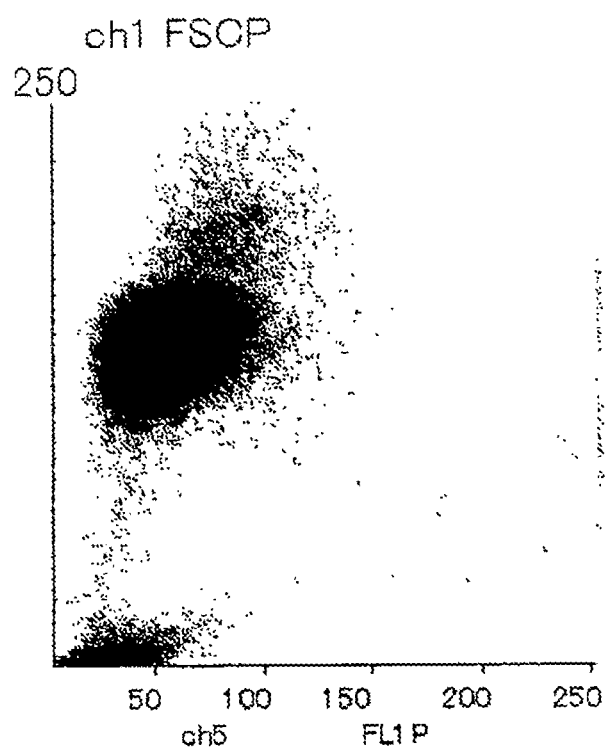
FIGS. 7A-7B show scattergrams obtained by the platelet measurement using the reagent for measuring platelets of Experimental Example 11.
Figure 7B:
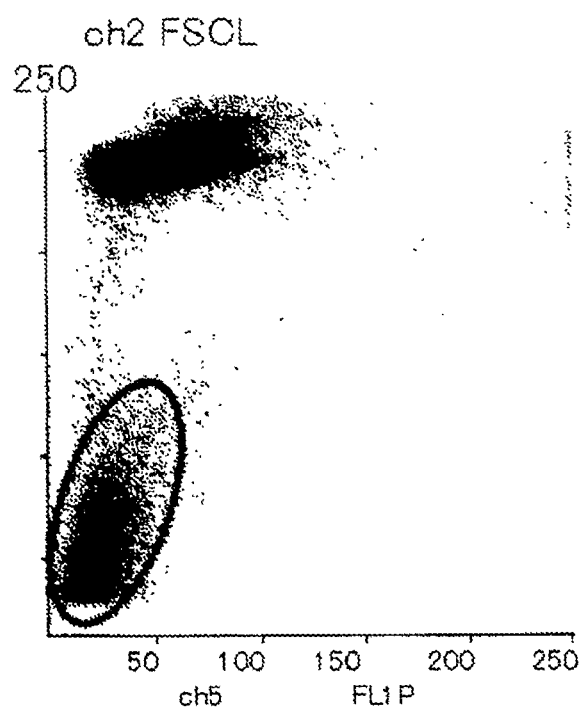
Figure 8A:
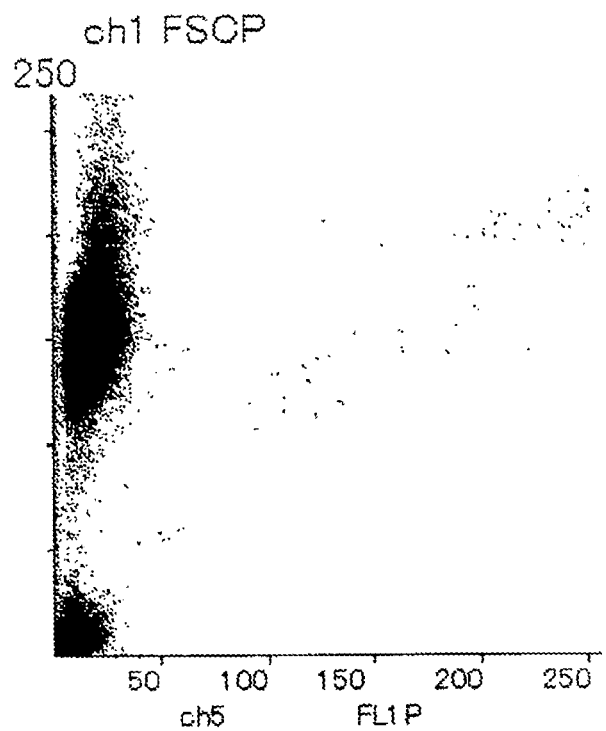
FIGS. 8A-8B show scattergrams obtained by the platelet measurement using the reagent for measuring platelets of Experimental Example 12.
Figure 8B:
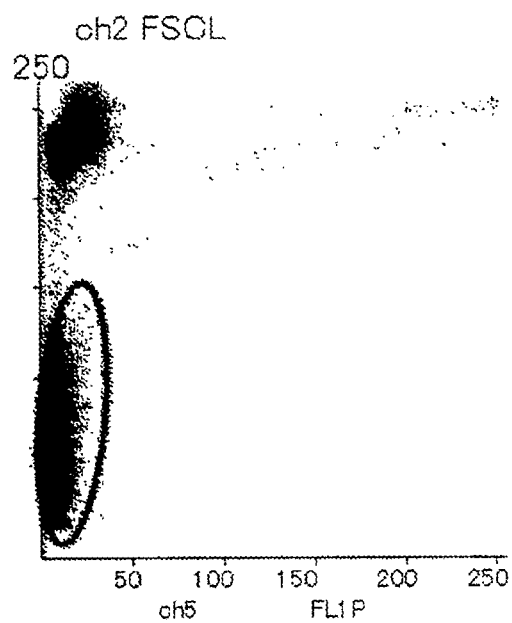
Figure 9A:
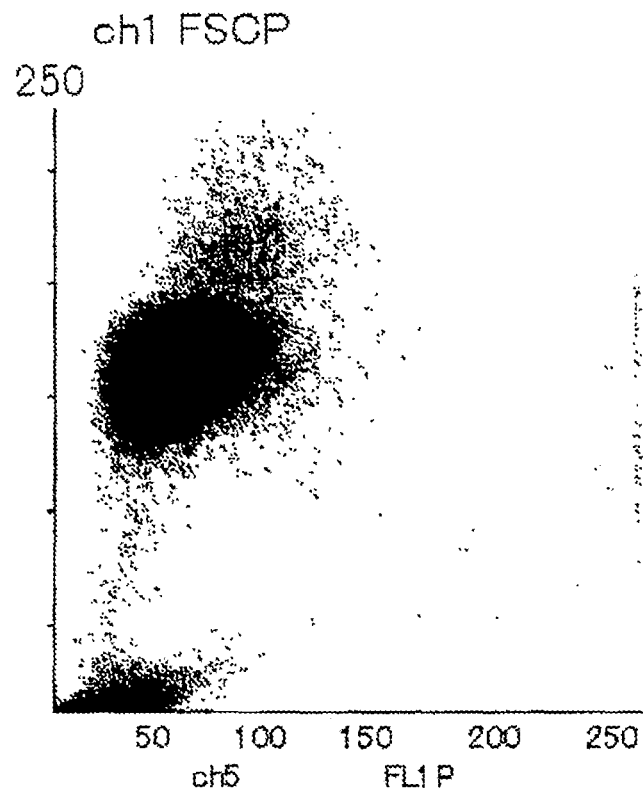
FIGS. 9A-9B show scattergrams obtained by the platelet measurement using the dye reagent of Experimental Example 13.
Figure 9B:
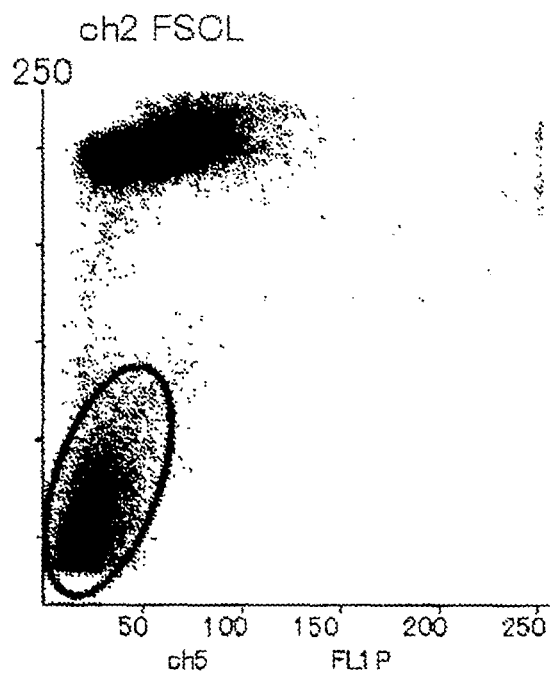

The constitution of the detecting section 5 equipped with a flow cytometer is now described with referring to FIG. 4. FIG. 4 is a schematic plan view showing the constitution of the detecting section. The detecting section 5 is provided with a semiconductor laser light source 52 so as to emit a laser beam towards a flow cell 51. Between the semiconductor laser light source 52 and the flow cell 51, Light application lenses 53 consisting of a plurality of lenses are provided. On a light axis extended linearly from the semiconductor laser light source 52, a beam stopper 54a is provided so as to be opposed to the light application lenses 53 across the flow cell 51, so that direct light from the semiconductor laser light source 52 is interrupted by the beam stopper 54a. On further downstream of the light axis from the beam stopper 54a, a photodiode 54 is provided.

When a measurement sample passes through the flow cell 51, scattered light and fluorescence signals are generated due to a laser beam. Among the signals, the forward signal light is emitted toward the photodiode 54. Among light beams which goes along the light axis linearly extended from the semiconductor laser light source 52, direct light from the semiconductor laser light source 52 is interrupted by the beam stopper 54a, and the photodiode 54 mainly receives scattered light which goes along the light source (hereinafter referred to as "forward scattered light"). The forward scattered light emitted from the flow cell 51 is photoelectrically transduced in the photodiode 54, and the thus generated electric signal (hereinafter referred to as "forward scattered light signal") is amplified in an amplifier 54b. The forward scattered light signal is output to the controlling section 4, further output to the data process unit 3 via the interface 7, and processed in the data analyzing section 9 of the data process unit 3.

Such forward scattered light signal reflects the size of particles to be detected. By processing the forward scattered light signal in the data analyzing section 9, the size of particles to be detected is obtained.

In the direction which crosses at right angles with the light axis linearly extended from the semiconductor laser light source 52 to the photodiode 54 is provided with a side condensing lens 55, so as to condense side light with the side condensing lens 55 which is generated by applying a semiconductor laser to particles to be detected passing through the flow cell 51 (light which is emitted to the direction crossing at right angles with the light axis). On the downstream of the side condensing lens 55 in the direction of the side light is provided with a dichroic mirror 56, so as to divide signal light received from the side condensing lens 55 into a scattered light component and a fluorescence component. On the side direction of the dichroic mirror 56 (the direction which crosses with the light axis connecting the side condensing lens 55 and the dichroic mirror 56) is provided with a photodiode 57 for receiving side scattered light, and on the downstream of the dicroic mirror 56 in the direction of the light axis are provided with an optical filter 58a and a photomultiplier 58. The side scattered light component divided in the dichroic mirror 56 is photoelectrically transduced in the photodiode 57, and the thus generated electric signal (hereinafter referred to as "side scattered light signal") is amplified in an amplifier 57a. The side scattered light signal is output to the controlling section 4, further output to the data process unit 3 via the interface 7, and processed in the data analyzing section 9 of the data process unit 3.

The side scattered light signal reflects internal information of particles to be detected (e.g. the nuclear size of leukocytes and the like). By processing the side scattered light signal in the data analyzing section 9, the nuclear size of leukocytes and the like are obtained.

The side fluorescence component emitted from the dichroic mirror 56 is selected depending on the wavelength in the optical filter 58a and photoelectrically transduced in the photomultiplier 58. The thus generated electric signal (side fluorescence signal) is amplified in an amplifier 58b. The side fluorescence signal is output to the controlling section 4, further output to the data process unit 3 via the interface, and processed in the data analyzing section 9 of the data process unit 3.

The side fluorescence signal reflects information on the degree of staining of particles to be detected. By processing the side fluorescence signal in the data analyzing section 9, the degree of staining of particles to be detected is obtained.

The data analyzing section 9 of the data process unit 3 can analyze the thus obtained forward scattered light signal, side scattered light signal and fluorescence signal to detect the particles to be detected, and further can count the detected particles. The data analyzing section 9 further generates scattergrams based on the analysis results of the forward scattered light signal, side scattered light signal and fluorescence signal. The generated scattergram are displayed in the display section 10.

By employing such sample analyzer, platelets can be measured.

First, in the sample preparing section 6, a sample is mixed with a reagent for measuring platelets or with reagents contained in a reagent kit for measuring platelets to prepare a measurement sample. The reagent and reagent kit for measuring platelets to be used can be the reagent and reagent kit for measuring platelets described above. In the reagent for measuring platelets or in the dye reagent of the reagent kit for measuring platelets contains Nile Blue, so that platelets contained in the sample are stained with Nile Blue.

In the sample preparing section 6, a measurement sample is preferably prepared by mixing a sample and the reagent for measuring platelets or the reagents contained in the reagent kit for measuring platelets so as to obtain the concentration of Nile Blue in the measurement sample of 0.05 to 5.0 ppm (0.00014 to 0.014 mmol/L), preferably 0.1 to 0.6 ppm, further preferably 0.2 to 0.5 ppm. The reaction temperature and time for preparing the measurement sample is preferably the ones described above for the reaction temperature and time for the reagent for measuring platelets.

The measurement sample prepared in the sample preparing section 6 is then provided to the detecting section 5. In the detecting section 5, the measurement sample is introduced into the flow cell 51 of the flow cytometer, and a laser beam is applied from the semiconductor laser light source 52 to the particles to be detected in the measurement sample. The forward scattered light signal, side scattered light signal and fluorescence signal obtained by applying the laser beam to the particles are processed in the data analyzing section 9 of the data process unit 3.

In the data analyzing section 9, platelets in the measurement sample are clearly distinguished from other components such as fractured red cells or lipid particles contained in the sample based on the forward scattered light signal and fluorescence signal. In data analyzing section 9, the thus detected platelets may also be counted. In order to detect and count platelets based on the forward scattered light signal and fluorescence signal, the signal processing in the data analyzing section 9 is preferably carried out by using an appropriate analyzing software.

In the above, the constitution in which platelets are detected based on the forward scattered light signal and fluorescence signal. However, other constitutions such as the one in which platelets are detected based on the side scattered light signal and fluorescence signal may be employed.

Examples

The present invention is now described in further details. However, these Examples are not intended to limit the scope of the present invention.

Experimental Examples 1 to 8

Storage Stability of Reagents for Measuring Platelets Containing Nile Blue Hydrogensulfate In order to demonstrate the storage stability of the dye reagent, reagents for measuring platelets (dye reagents) which contain Nile blue shown in Table 1 at the concentrations shown in Table 1 were prepared, and absorbance, a parameter reflecting the effective dye component concentration of Nile Blue in the dye reagents, was measured to evaluate the storage stability of Nile Blue in the dye reagents.

Reagents for Measuring Platelets:

| Dye | At the concentrations shown in Table 1 |
|---|---|
| Ethylene glycol | 5 mL |

TABLE 1

| Experimental Examples | Dye | Concentration |
|---|---|---|
| 1 | Nile Blue hydrogensulfate (Nile Blue hydrogensulfate, Wako Pure Chemical Industries, Ltd.) | 18.4 ppm |
| 2 | Nile Blue hydrogensulfate (Nile Blue hydrogensulfate, Kishida Chemical Co., Ltd.) | 18.4 ppm |
| 3 | Nile Blue sulfate (Nile Blue sulfate salt, Sigma) | 16.0 ppm |
| 4 | Nile Blue sulfate (Nile Blue, Wako Pure Chemical Industries, Ltd.) | 16.0 ppm |
| 5 | Nile Blue sulfate (Nile Blue sulfate, Nacalai Tesque, Inc.) | 16.0 ppm |
| 6 | Nile Blue sulfate (Nile Blue A, Nacalai Tesque, Inc.) | 16.0 ppm |
| 7 | Nile Blue chloride (Nile Blue chloride, Kishida Chemical Co., Ltd.) | 16.0 ppm |
| 8 | Nile Blue sulfate (Nile Blue A, Kishida Chemical Co., Ltd.) | 16.0 ppm |

The obtained dye reagents were diluted to 1/10 with ethanol, and absorbance of each dye reagent was measured at 630 nm with a spectrophotometer, at which the absorbance spectrum of the dye is maximum. The absorbance measurements were carried out with using ethanol as a reference. Absorbance of the diluted reagents was measured after 2-, 4- and 7-month storages at 45° C., and the rates of change in absorbance were calculated. The results of the absorbance measurements and the rates of change in absorbance are shown in Tables 2-1 and 2-2, respectively.

The "rate of change in absorbance" denotes the rate of change in absorbance by percent calculated by using the maximum measured absorbance value as a standard value among all absorbance values obtained for the respective Experimental Example.

TABLE 2-1

| Experimental Example | Immediately after dilution | 2 months later | 4 months later | 7 months later |
|---|---|---|---|---|
| 1 | 0.3223 | 0.3141 | 0.3063 | 0.3001 |
| 2 | 0.3369 | 0.3250 | 0.3138 | 0.2799 |
| 3 | 0.3316 | 0.2919 | 0.2583 | 0.2285 |
| 4 | 0.3297 | 0.2803 | 0.2484 | 0.2178 |
| 5 | 0.3217 | 0.2729 | 0.2441 | 0.2117 |
| 6 | 0.3248 | 0.2790 | 0.2443 | 0.2119 |
| 7 | 0.3184 | 0.2696 | 0.2335 | 0.2023 |
| 8 | 0.3319 | 0.2825 | 0.2426 | 0.2234 |

TABLE 2-2

| Experimental Example | Immediately after dilution | 2 months later | 4 months later | 7 months later |
|---|---|---|---|---|
| 1 | 0.0% | −2.5% | −5.0% | −6.9% |
| 2 | 0.0% | −3.5% | −6.9% | −16.9% |
| 3 | 0.0% | −12.0% | −22.1% | −31.1% |
| 4 | 0.0% | −15.0% | −24.7% | −33.9% |
| 5 | 0.0% | −15.2% | −24.1% | −34.2% |
| 6 | 0.0% | −14.1% | −24.8% | −35.0% |
| 7 | 0.0% | −15.3% | −26.7% | −36.5% |
| 8 | 0.0% | −14.9% | −26.9% | −32.7% |

As shown in Table 2-2, reduction in absorbance of the dye reagent of Experimental Example 1 which contained Nile Blue hydrogensulfate as the dye was 2.5%, 5.0% and 6.9% after 2 months, 4 months and 7 months, respectively. Reduction in absorbance of the dye reagent of Experimental Example 2 which also contained Nile Blue hydrogensulfate as the dye was 3.5%, 6.9% and 16.9% after 2 months, 4 months and 7 months, respectively.

On the other hand, absorbance of the dye reagents of Experimental Examples 3 to 8 which contained Nile Blues having counter ions other than hydrogensulfate ion was decreased by more than 10%, more than 20% and more than 30% after 2 months, 4 months and 7 months, respectively.

From the comparisons with these Experimental Examples 3 to 8, it is found that the dye reagents which contain Nile Blues having hydrogensulfate ions as counter ions have less reduction in absorbance with time and superior storage stability compared to the dye reagents which contain Nile Blues having counter ions other than hydrogensulfate ion.

Experimental Examples 9 to 13

Platelet Staining Property of Reagents for Measuring Platelets Comprising Nile Blue Hydrogensulfate The following experiments were carried out in order to demonstrate the platelet staining property of the reagents for measuring platelets comprising Nile Blue hydrogensulfate.

Reagent kits consisting of dye reagents having the following compositions and the dilution reagent were prepared.

| (1) Dye reagents | |
|---|---|
| Dye for staining platelets | At the concentrations shown in Table 3 |
| Ethylene glycol | 1 L |
| (2) Dilution reagent | |
| Tricine (buffering agent) | 1.8 g |
| Lauryltrimethylammonium chloride (LTAC) | 0.15 g |
| Purified water | 1 L |
| (adjusted to pH 9.0 and osmotic pressure 200 mOsm/kg.H2O) | |

The dyes for measuring platelets used were those shown in Table 3 at the concentrations shown in Table 3. The final concentrations of the dyes after mixing the reagents with a sample are shown in parentheses.

The chemical formulae of the dyes are shown in Table 3.

The dilution reagent (1 mL aliquots) in tubes was heated in a water bath of 40° C. To the dilution reagent were added 20 μl of the dye reagent and 5 μl of whole blood of healthy human as a sample, and the reaction was carried out at 40° C. for 25 seconds to prepare measurement samples. The measurement samples were introduced into a detecting section of a flow cytometer having a light source emitting light with the wavelength of 633 nm, excitation light was applied to the cells in the measurement samples, a scattered light signal and fluorescence signal emitted from the cells were detected, the obtained signals were analyzed and the platelets in the measurement samples were measured. Preparation of measurement samples and measurements of platelets by flow cytometer were carried out in the blood analyzer XE-2100 (Sysmex Corporation). The output of the light source of the blood analyzer was modified to 9 W from the normal output of 3 W.

TABLE 3

| | Dye | Conc. | Structure | Results |
|---|---|---|---|---|
| Ex. 9 | Nile Blue A Hydrogensulfate (Wako Pure Chemicals) | 18.4 ppm (0.3 ppm) | $HSO_4^-$ ; $H_2N$-...-$O$-...-$N^+(CH_2CH_3)_2$ | Sufficient staining of platelets |
| Ex. 10 | Nile Blue A Hydrogensulfate (Kishida Chemical) | 18.4 ppm (0.3 ppm) | $HSO_4^-$ ; $H_2N$-...-$O$-...-$N^+(CH_2CH_3)_2$ | Sufficient staining of platelets |

TABLE 3-continued

| Dye | | Conc. | Structure | Results |
|---|---|---|---|---|
| Ex. 11 | Methylene Blue NNX (Sigma) | 102.5 ppm (2 ppm) | [structure shown] | Insufficient staining of platelets |
| Ex. 12 | Cresyl Violet Acetate (Sigma) | 1025 ppm (20 ppm) | [structure shown] | No staining |
| Ex. 13 | Basic Green 5 (Tokyo Chemical Industry) | 1025 ppm (20 ppm) | [structure shown] | Insufficient staining of platelets |

The scattergrams obtained from Experimental Examples 9 to 13 are shown in FIGS. 5 to 9, and their subsections (i.e., 5A, 5B, etc.), respectively. In each Figure, (a) is a scattergram having the y-axis of forward scattered light intensity and the x-axis of fluorescence intensity, and (b) is a scattergram in which the y-axis of the scattergram (a) is converted to the logarithms. In (b), the area where platelets appear is shown with a solid line. The measurement results from the Experimental Examples are shown in Table 3.

As shown in FIGS. 5 to 9, when Experimental Examples 9 and 10 were used which contained Nile Blue hydrogensulfate as the dye for staining platelets, platelets were stained sufficiently compared to Experimental Examples 11 to 13 which contained the dyes other than Nile Blue, so that platelets could be detected in the region with higher fluorescence intensity.

Thus, when Nile Blue hydrogensulfate is used as the dye for staining platelets, platelets can be measured with better discrimination from other blood cell components.

Next, it was examined whether platelets can be specifically stained by using the dye reagents of Experimental Examples 9 and 10 containing Nile Blue hydrogensulfate even when blood contains the contaminants such as lipid particles.

The platelet measurements of blood containing fragmented red cells and blood containing lipid particles were carried out with the dye reagents of Experimental Examples 9 and 10. The experimental procedures were the same as above except that the blood containing fragmented red cells and the blood containing lipid particles were used instead of whole blood of healthy human.

Figure 10A:
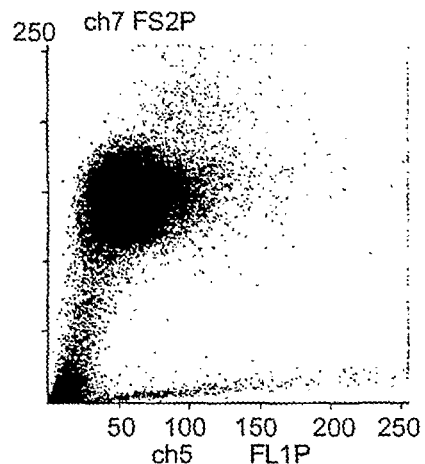
FIGS. 10A-10C show scattergrams obtained by the measurement of blood containing fragmented red cells using the reagent for measuring platelets of Experimental Example 9.
Figure 10B:
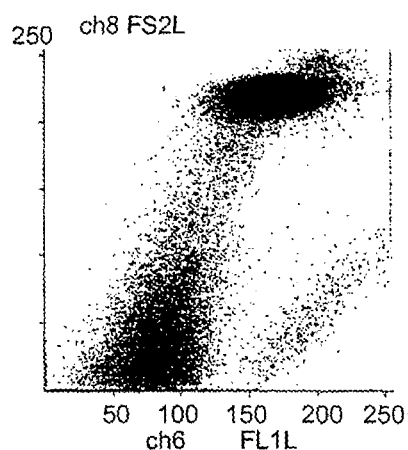
Figure 10C:
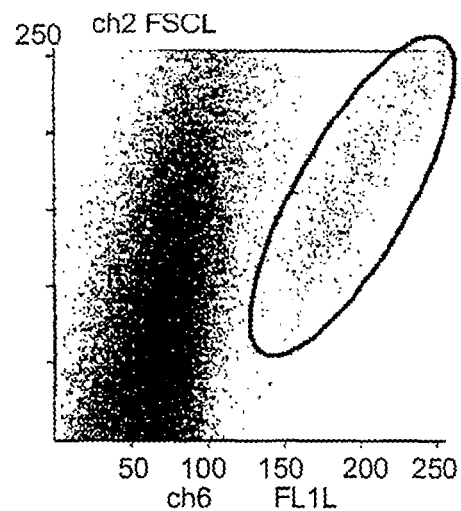
Figure 11A:
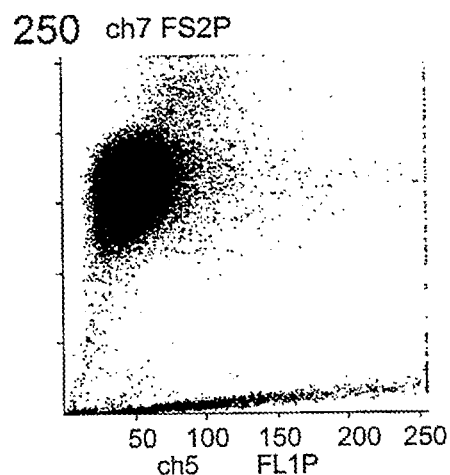
FIGS. 11A-11C show scattergrams obtained by the measurement of blood containing lipid particles using the reagent for measuring platelets of Experimental Example 9.
Figure 11B:
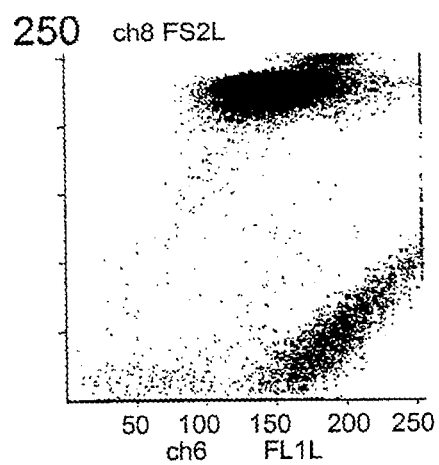
Figure 11C:
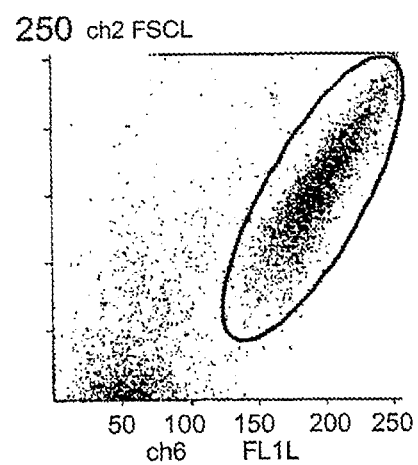
Figure 12A:
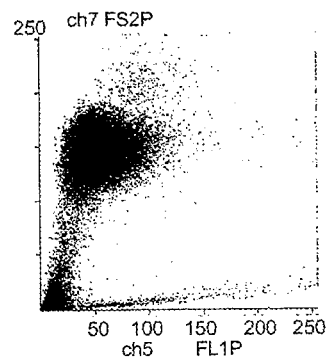
FIGS. 12A-12C show scattergrams obtained by the measurement of blood containing fragmented red cells using the reagent for measuring platelets of Experimental Example 10.
Figure 12B:
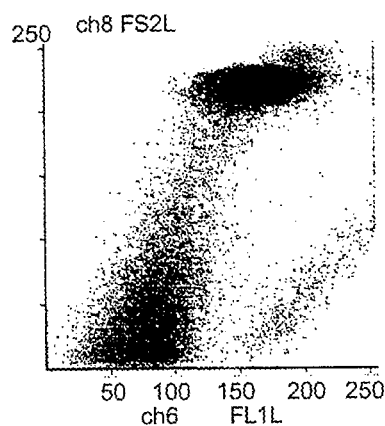
Figure 12C:
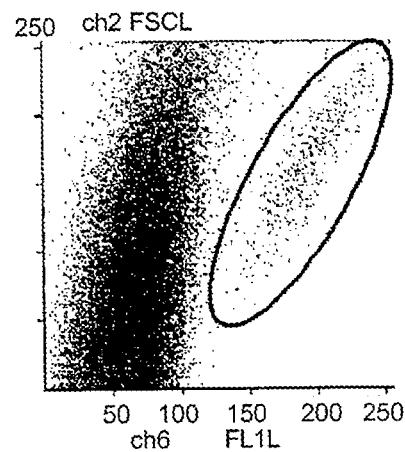
Figure 13A:
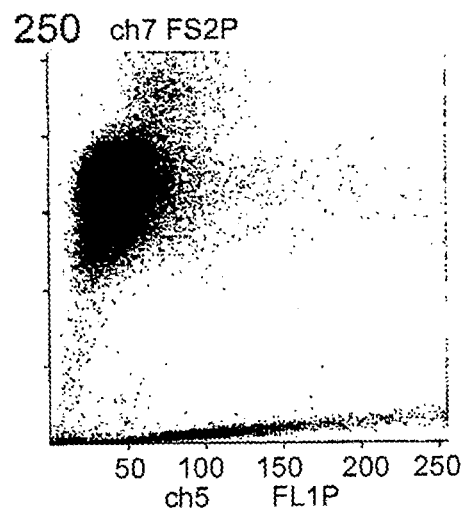
FIGS. 13A-13C show scattergrams obtained by the measurement of blood containing lipid particles using the reagent for measuring platelets of Experimental Example 10.
Figure 13B:
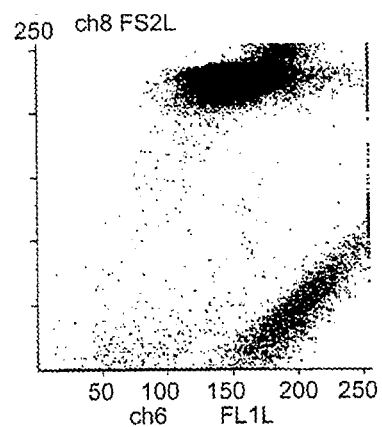
Figure 13C:
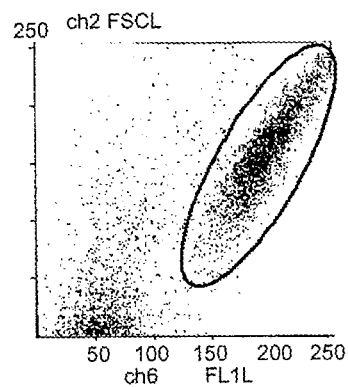
Figure 14A:
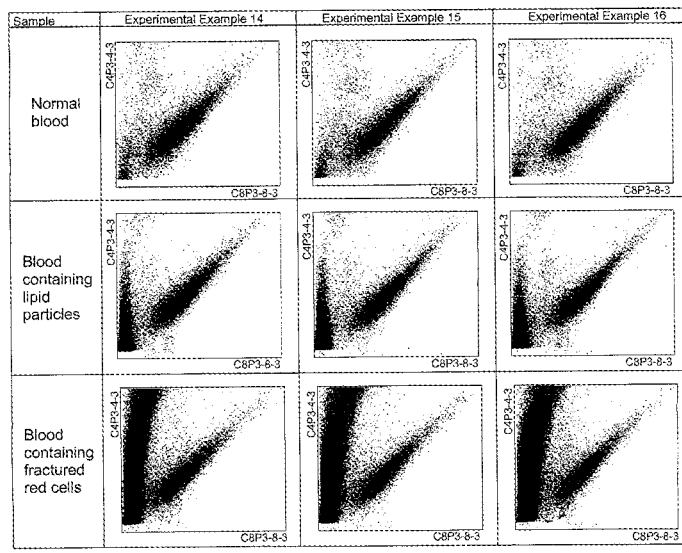
FIGS. 14A-14D show scattergrams obtained by the measurements of samples using the reagents for measuring platelets of Experimental Examples 14 to 24.
Figure 14B:
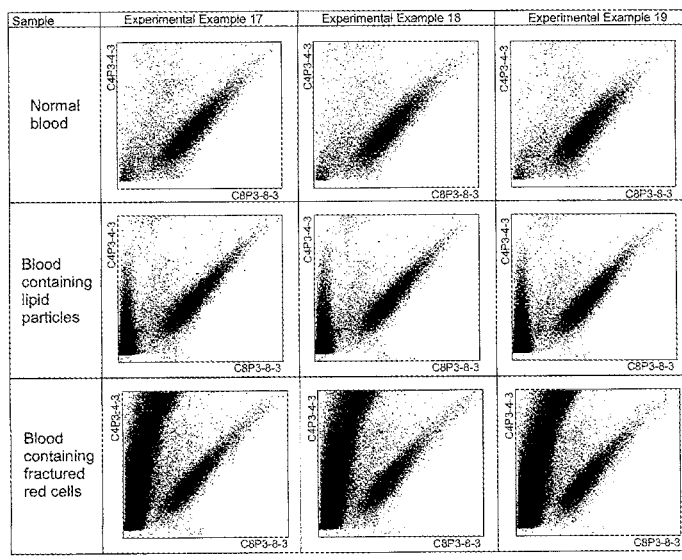
Figure 14C:
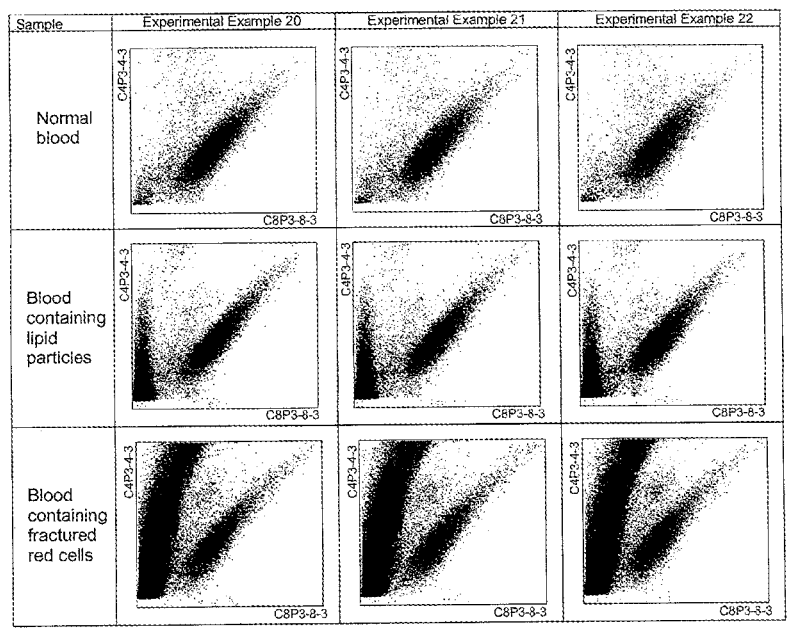
Figure 14D:
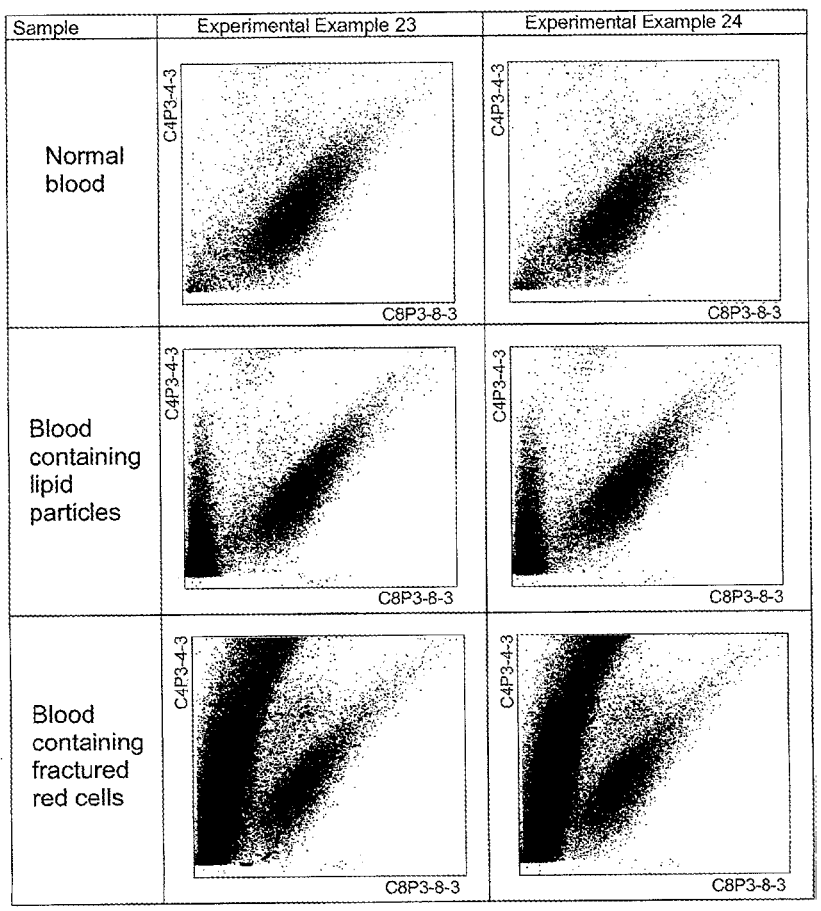

The scattergrams obtained from the measurements of blood containing fragmented red cells and blood containing lipid particles using the dye reagent of Experimental Example 9 are shown in FIGS. 10 and 11, and their subsections. The scattergrams obtained from the measurements of blood containing fragmented red cells and blood containing lipid particles using the dye reagent of Experimental Example 10 are shown in FIGS. 12 and 13, and their subsections. In each Figure, (a) is a scattergram having the y-axis of forward scattered light intensity and the x-axis of fluorescence intensity, (b) is a scattergram in which the y-axis of the scattergram (a) is converted to the logarithms, and (c) is a magnified view of the area where platelets appear in (b). In (c), the area where platelets appear is shown with a solid line.

The results of FIGS. 10 to 13, and their subsections, show that the dye reagents of Experimental Examples 9 and 10 can specifically stain platelets with clear discrimination from fragmented red cells or lipid particles in blood. Thus, when Nile Blue hydrogensulfate is used for staining platelets, platelets can be measured with clear discrimination from other blood cell components, even when blood contains contaminants such as fragmented red cells or lipid particles.

According to Experimental Examples 1 and 2, it is shown that the dye reagents containing Nile Blue hydrogensulfate have less reduction in absorbance with time and superior storage stability. Further, Experimental Examples 9 and 10 show that Nile Blue hydrogensulfate as the dye for staining platelets can specifically stain platelets in blood, and that it makes it possible to carry out accurate platelet measurements even when blood contains contaminants such as fragmented red cells or lipid particles.

Experimental Examples 14 to 24

Platelet Staining Properties of Reagents for Measuring Platelets Containing Nile Blue Hydrogensulfates at Various Concentrations The dye reagents were prepared containing Nile Blue hydrogensulfate (Merck Co.) at the concentrations indicated in Table 4 in ethylene glycol.

The obtained dye reagents were combined with the dilution reagent described in Experimental Examples 9 to 13 to measure platelets in the following samples: whole blood of healthy human, blood containing fragmented red cells and blood containing lipid particles, as similar to Experimental Examples 9 to 13.

TABLE 4

| Experimental Example | Dye concentration in dye reagent (mg/L) | Final dye concentration in the mixture of reagents and sample (mg/L) |
|---|---|---|
| 14 | 6.0 | 0.12 |
| 15 | 8.0 | 0.16 |
| 16 | 9.1 | 0.18 |
| 17 | 12.5 | 0.24 |
| 18 | 15.0 | 0.29 |
| 19 | 16.6 | 0.32 |
| 20 | 18.3 | 0.36 |
| 21 | 20.3 | 0.40 |
| 22 | 22.5 | 0.44 |
| 23 | 25.5 | 0.50 |
| 24 | 29.3 | 0.57 |

The obtained scattergrams are shown in FIGS. 14A-14D.

The results in FIGS. 14A-14D show that platelets were sufficiently measured with Nile Blue hydrogensulfate at all concentrations tested.

Among these, when the sample, blood containing fragmented red cells, was tested with the reagents for measuring platelets of Experimental Examples 17 to 22 (final concentration of Nile Blue hydrogensulfate: 0.24 to 0.44 mg/L), platelets were more clearly discriminated from other blood cell components and contaminants.

Experimental Example 25

Storage Stability of Reagents for Measuring Platelets Containing Nile Blue Hydrogensulfate The dye reagent was prepared containing 14.4 ppm of Nile Blue hydrogensulfate (Merck Co.) in ethylene glycol. The dye reagent was stored at the temperature condition of 45° C. for 16 weeks and used for the measurement of samples.

The samples used were blood taken from healthy human, low-platelet blood, blood containing artificial lipid and blood containing fragmented red cells. Platelets were measured as described in Experimental Examples 9 to 13.

Figure 15:
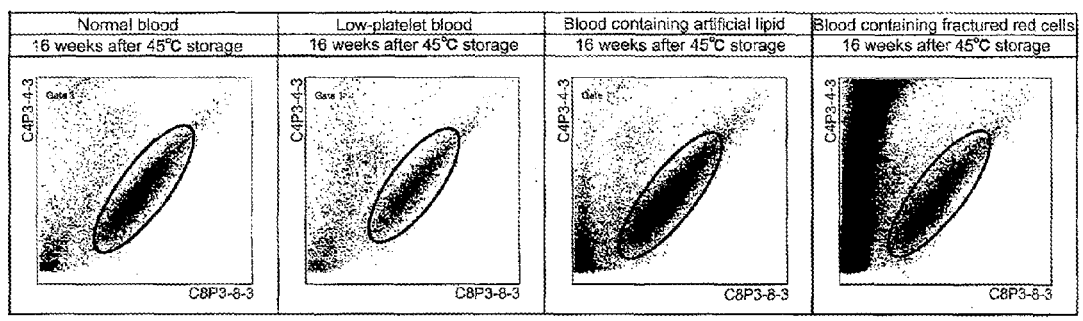
FIG. 15 shows scattergrams obtained by the measurement of a sample using the reagent for measuring platelets of Experimental Example 25.

The obtained scattergrams are shown in FIG. 15.

The scattergrams in FIG. 15 show that platelets could be measured with clear discrimination from contaminants in all samples.

These results show that, when Nile Blue hydrogensulfate is used as the dye for staining platelets, platelets can be accurately measured with little effect from contaminants, even when the dye reagent is stored under unfavorable condition for the dye.

The change in concentration of the dye during the storage under the above condition was examined by the following experiments.

Absorbance was measured as described in Experimental Examples 1 to 8 except that the dye reagent immediately after preparation and the dye reagent after 16-week storage were diluted to 1/10 with ethanol and absorbance at 628 nm was measured. Based on the reduction rate in the measured absorbance, the dye concentration in the dye reagent after 16-week storage was calculated. The results are shown in the following Table 5.

TABLE 5

|  | Immediately after preparation | After 16-week storage |
|---|---|---|
| Absorbance | 0.288 | 0.262 |
| Reduction rate (%) | 0.00% | −9.03% |

TABLE 5-continued

|  | Immediately after preparation | After 16-week storage |
|---|---|---|
| Dye concentration (ppm) | 14.40 | 13.10 |

As shown in Table 5, the dye concentration in the undiluted solution after 16-week storage was calculated as 13.1 ppm. Therefore, it is shown that a favorable dye concentration for platelet measurements can be maintained even after the storage under the above condition.

Experimental Examples 26 to 29

Storage Stability of Reagents for Measuring Platelets Containing Nile Blue and Acid The experiments were carried out in order to study the storage stability of Nile Blue solutions containing hydrochloric acid or sodium hydroxide. The storage stability of the Nile Blue solutions was evaluated by measuring absorbance which is a parameter reflecting the effective dye component concentration of Nile Blue in the solution.

In the following descriptions, the "rate of change in absorbance" denotes the rate of change in absorbance by percent calculated by using the maximum measured absorbance value as a standard value among all absorbance values obtained from the respective Experimental Example.

In the present Experimental Examples, Nile Blue having sulfuric ion as a counter ion (Nile Blue A, Sigma) was used. This Nile Blue was dissolved in ethylene glycol at the concentration of 0.02 mmol/L to prepare Nile Blue solution (Comparative Example 1).

To 5 mL of the Nile Blue solution was added the following substance at the following concentration to obtain Experimental Examples 26 to 29.

Experimental Example

| 26 | Hydrochloric acid | 2 mmol/L |
| 27 | Hydrochloric acid | 0.02 mmol/L |
| 28 | Sodium hydroxide | 2 mmol/L |
| 29 | Sodium hydroxide | 0.02 mmol/L |

Each solution was diluted to 1/5 with ethanol, and absorbance of each solution was measured at 630 nm with a spectrophotometer, at which the absorbance spectrum of the dye is maximum. The diluted solutions were stored under the temperature condition of 60° C., and absorbance at 2 weeks and 4 weeks after dilution was measured to calculate the rate of change in absorbance. Ethanol was used as a control in the measurement of absorbance. The results of absorbance measurements and the rates of change in absorbance are shown in Tables 6-1 and 6-2, respectively.

TABLE 6-1

|  |  | Immediately after preparation | After 2 weeks | After 4 weeks |
|---|---|---|---|---|
| Comparative Example 1 |  | 0.5158 | 0.5033 | 0.4306 |
| Experimental Example | 26 (HCl 2 mM) | 0.5388 | 0.0800 | 0.0055 |
|  | 27 (HCl 0.02 mM) | 0.5319 | 0.5286 | 0.4741 |
|  | 28 (NaOH 2 mM) | 0.0065 | 0.0017 | 0.0047 |
|  | 29 (NaOH 0.02 mM) | 0.4948 | 0.4721 | 0.3825 |

TABLE 6-2

|  |  | Immediately after preparation | After 2 weeks | After 4 weeks |
|---|---|---|---|---|
| Comparative Example 1 |  | 0.0% | −2.4% | −16.5% |
| Experimental Example | 26 (HCl 2 mM) | 0.0% | −85.2% | −99.0% |
|  | 27 (HCl 0.02 mM) | 0.0% | −0.6% | −10.9% |
|  | 28 (NaOH 2 mM) | 0.0% | −73.8% | −27.7% |
|  | 29 (NaOH 0.02 mM) | 0.0% | −4.6% | −22.7% |

As shown in Table 6-1, initial absorbance of Comparative Example 1 was 0.5158 to which hydrochloric acid or sodium hydroxide was not added. The rates of change in absorbance of Comparative Example 1 were, as shown in Table 6-2, −2.4% and −16.5% at 2 and 4 weeks after the preparation, respectively.

The initial absorbances of Experimental Examples 26 and 27 containing hydrochloric acid were, as shown in Table 6-1, 0.5388 and 0.5319, respectively, and these values were not significantly different from the initial absorbance of Comparative Example 1.

The rates of change in absorbance of Experimental Example 26 containing 2 mmol/L concentration of hydrochloric acid were −85.2% and −99.0% at 2 and 4 weeks, presenting significant reduction in absorbance with time compared to Comparative Example 1. This shows that the storage stability of Nile Blue solutions was lowered.

On the other hand, the rates of change in absorbance of Experimental Example 27 containing 0.02 mmol/L concentration of hydrochloric acid were −0.6% and −10.9% at 2 and 4 weeks, showing that the reduction in absorbance with time was moderate compared to Comparative Example 1. This shows that the storage stability of Nile Blue solutions was improved.

The initial absorbances of Experimental Examples 28 and 29 containing sodium hydroxide were, as shown in Table 6-1, 0.0065 and 0.4948, respectively, showing that the initial absorbance was lowered compared to Comparative Example 1.

The rates of change in absorbance of Experimental Examples 28 and 29 were, as shown in Table 6-2, below −20% at 4 weeks after preparation, showing that the reduction in absorbance with time was significant. This shows that the storage stability of Nile Blue solutions was lowered.

These experimental results suggested that the addition of hydrochloric acid at certain concentrations to Nile Blue solutions may improve the storage stability of the Nile Blue solutions.

Experimental Examples 30 to 36

Effect of Molar Concentration Ratio Between Nile Blue and Hydrochloric Acid on Storage Stability of Reagents for Measuring Platelets It is found that the storage stability of Nile Blue solutions is improved by adding a certain concentration of hydrochloric acid, according to Experimental Examples 26 to 29.

It is considered that the reduction in the storage stability of Nile Blue solutions, namely, the reduction in the effective dye component concentration of Nile Blue is due to the degradation of the effective dye component, so that the concentration of hydrochloric acid to be added to the solutions should be examined in relation to the number of molecules of Nile Blue.

Thus, in the present Experimental Examples, the relations between the ratio of Nile Blue and hydrochloric acid (molar concentration ratio) and the storage stability of Nile Blue solutions were examined by varying the ratio of hydrochloric acid and Nile Blue (molar concentration ratio) in Nile Blue solutions.

The storage stability of Nile Blue solutions is examined by evaluating absorbance of Nile Blue solutions as similar to Experimental Examples 26 to 29.

As similar to Experimental Examples 26 to 29, Nile Blue A (Sigma) was dissolved in ethylene glycol at the concentration of 0.02 mmol/L to prepare Nile Blue solution (Comparative Example 2).

To 5 mL of the Nile Blue solution was added hydrochloric acid at the following concentration to obtain Experimental Examples 30 to 36. The molar concentration ratios between Nile Blue and hydrochloric acid in the solutions are described in parentheses.

Experimental Example

| 30 | Hydrochloric acid | 0.002 mmol/L (10:1) |
| 31 | Hydrochloric acid | 0.006 mmol/L (3:1) |
| 32 | Hydrochloric acid | 0.02 mmol/L (1:1) |
| 33 | Hydrochloric acid | 0.06 mmol/L (1:3) |
| 34 | Hydrochloric acid | 0.2 mmol/L (1:10) |
| 35 | Hydrochloric acid | 0.6 mmol/L (1:30) |
| 36 | Hydrochloric acid | 2 mmol/L (1:100) |

The obtained dye solutions were diluted to 1/20 with ethanol and absorbance of each solution was measured at 630 nm with a spectrophotometer, at which the absorbance spectrum of the dye is maximum. The dye solutions were stored under the temperature condition of 45° C., and absorbance at 4 weeks, 9 weeks and 18 weeks after the preparation was measured to calculate the rate of change in absorbance. Ethanol was used as a control in the measurement of absorbance.

The results of absorbance measurements and the rates of change in absorbance are shown in Tables 7-1 and 7-2, respectively.

TABLE 7-1

|  |  | Immediately after preparation | After 4 weeks | After 9 weeks | After 18 weeks |
|---|---|---|---|---|---|
| Comparative Example 2 |  | 0.1342 | 0.1208 | 0.1174 | 0.0986 |
| Experimental Example | 30 (HCl 0.002 mM) | 0.1369 | 0.1246 | 0.1225 | 0.1051 |
|  | 31 (HCl 0.006 mM) | 0.1371 | 0.1277 | 0.1244 | 0.1084 |
|  | 32 (HCl 0.02 mM) | 0.1380 | 0.1303 | 0.1308 | 0.1148 |
|  | 33 (HCl 0.06 mM) | 0.1381 | 0.1211 | 0.0838 | 0.0245 |
|  | 34 (HCl 0.2 mM) | 0.1394 | 0.0255 | 0.0001 | 0.0000 |
|  | 35 (HCl 0.6 mM) | 0.1399 | 0.0282 | 0.0006 | 0.0000 |
|  | 36 (HCl 2 mM) | 0.1399 | 0.0466 | 0.0014 | 0.0000 |

TABLE 7-2

|  |  | Immediately after preparation | After 4 weeks | After 9 weeks | After 18 weeks |
|---|---|---|---|---|---|
| Comparative Example 2 |  | 0.0% | −10.0% | −12.5% | −26.5% |
| Experimental Example | 30 (HCl 0.002 mM) | 0.0% | −9.0% | −10.5% | −23.2% |
|  | 31 (HCl 0.006 mM) | 0.0% | −6.9% | −9.3% | −20.9% |
|  | 32 (HCl 0.02 mM) | 0.0% | −5.6% | −5.2% | −16.8% |
|  | 33 (HCl 0.06 mM) | 0.0% | −12.3% | −39.3% | −82.3% |
|  | 34 (HCl 0.2 mM) | 0.0% | −81.7% | −99.9% | −100.0% |
|  | 35 (HCl 0.6 mM) | 0.0% | −79.8% | −99.6% | −100.0% |
|  | 36 (HCl 2 mM) | 0.0% | −66.7% | −99.0% | −100.0% |

As shown in Table 7-1, initial absorbance of Comparative Example 2 was 0.1342 to which no hydrochloric acid was added. The rates of change in absorbance of Comparative Example 2 were, as shown in Table 7-2, −10.0%, −12.5% and −26.5% at 4, 9 and 18 weeks after the preparation, respectively.

The initial absorbances of Experimental Examples 30 to 36 were not significantly different from that of Comparative Example 2, as shown in Table 7-1.

The rates of change in absorbance of Experimental Example 30 in which the molar concentration ratio between Nile Blue and hydrochloric acid was 10:1 were −9.0%, −10.5% and −23.2% at 4, 9 and 18 weeks after the preparation, respectively.

The rates of change in absorbance of Experimental Example 31 in which the molar concentration ratio between Nile Blue and hydrochloric acid was 3:1 were −6.9%, −9.3% and −20.9% at 4, 9 and 18 weeks after the preparation, respectively.

The rates of change in absorbance of Experimental Example 32 in which the molar concentration ratio between Nile Blue and hydrochloric acid was 1:1 were −5.6%, −5.2% and −16.8% at 4, 9 and 18 weeks after the preparation, respectively.

As apparent from the comparison to Comparative Example 2, the reduction in absorbance of Experimental Examples 30 to 32 in which the molar concentration of hydrochloric acid is lower than that of Nile Blue is moderate at any point of time than Comparative Example 2 which does not contain hydrochloric acid. Thus, the storage stability of the Nile Blue solutions is improved.

In particular, Experimental Example 32 in which the molar concentration ratio between Nile Blue and hydrochloric acid was 1:1 had better storage stability than other Experimental Examples.

Experimental Examples 37 to 44

Storage Stability of Reagents for Measuring Platelets Containing Nile Blue and Sulfuric Acid Next, the storage stability of the Nile Blue solutions was studied which contained sulfuric acid instead of hydrochloric acid.

As similar to Experimental Examples 26 to 36, Nile Blue A (Sigma) was dissolved in ethylene glycol at the concentration of 0.02 mmol/L to prepare Nile Blue solution (Comparative Example 3).

To 5 mL of the Nile Blue solution was added sulfuric acid at the following concentration to obtain Experimental Examples 37 to 40. The molar concentration ratios between Nile Blue and sulfuric acid in the solutions are described in parentheses.

Experimental Example

| 37 | Sulfuric acid | 0.005 mmol/L (4:1) |
| 38 | Sulfuric acid | 0.01 mmol/L (2:1) |
| 39 | Sulfuric acid | 0.02 mmol/L (1:1) |
| 40 | Sulfuric acid | 0.05 mmol/L (1:2.5) |

Nile Blue solutions were prepared with Nile Blue A having sulfuric ion as a counter ion (Nacalai Tesque, Inc.) instead of Nile Blue A (Sigma) used in Experimental Examples 37 to 40 (Comparative Example 4).

To 5 mL of the Nile Blue solution was added sulfuric acid at the following concentration to obtain Experimental Examples 41 to 44. The molar concentration ratios between Nile Blue and sulfuric acid in the solutions are described in parentheses.

Experimental Example

| 41 | Sulfuric acid | 0.005 mmol/L (4:1) |
| 42 | Sulfuric acid | 0.01 mmol/L (2:1) |
| 43 | Sulfuric acid | 0.02 mmol/L (1:1) |
| 44 | Sulfuric acid | 0.05 mmol/L (1:2.5) |

The absorbances immediately after preparation of the solutions of Experimental Examples 37 to 44 were measured. Each solution was stored under the temperature condition of 45° C., and the absorbance at 1 month, 2 months, 3 months and 4 months after the preparation was measured to calculate the rate of change in absorbance.

The results of absorbance measurements and the rates of change in absorbance of Experimental Examples 37 to 40 are shown in Tables 8-1 and 8-2, respectively.

The results of absorbance measurements and the rates of change in absorbance of Experimental Examples 41 to 44 are shown in Tables 9-1 and 9-2, respectively.

TABLE 8-1

|  |  | Immediately after preparation | After 1 month | After 2 months | After 3 months | After 4 months |
| --- | --- | --- | --- | --- | --- | --- |
| Comparative Example 3 |  | 0.2852 | 0.2849 | 0.2421 | 0.2225 | 0.2076 |
| Experimental Example | 37 ($H_2SO_4$ 0.005 mM) | 0.2887 | 0.2907 | 0.2547 | 0.2367 | 0.2224 |
|  | 38 ($H_2SO_4$ 0.01 mM) | 0.2923 | 0.3045 | 0.3041 | 0.2672 | 0.2545 |
|  | 39 ($H_2SO_4$ 0.02 mM) | 0.2999 | 0.3109 | 0.3009 | 0.2980 | 0.3000 |
|  | 40 ($H_2SO_4$ 0.05 mM) | 0.3076 | 0.2921 | 0.2934 | 0.2123 | 0.1546 |

TABLE 8-2

|  |  | Immediately after preparation | After 1 month | After 2 months | After 3 months | After 4 months |
| --- | --- | --- | --- | --- | --- | --- |
| Comparative Example 3 |  | 0.0% | −0.1% | −15.1% | −22.0% | −27.2% |
| Experimental Example | 37 ($H_2SO_4$ 0.005 mM) | 0.0% | 0.7% | −11.8% | −18.0% | −23.0% |
|  | 38 ($H_2SO_4$ 0.01 mM) | 0.0% | 4.2% | 4.0% | −8.6% | −12.9% |
|  | 39 ($H_2SO_4$ 0.02 mM) | 0.0% | 3.7% | 0.3% | −0.6% | 0.0% |
|  | 40 ($H_2SO_4$ 0.05 mM) | 0.0% | −5.0% | −4.6% | −31.0% | −49.7% |

TABLE 9-1

|  | | Immediately after preparation | After 1 month | After 2 months | After 3 months | After 4 months |
|---|---|---|---|---|---|---|
| Comparative Example 4 | | 0.2941 | 0.2901 | 0.2552 | 0.2449 | 0.2136 |
| Experimental Example | 41 ($H_2SO_4$ 0.005 mM) | 0.2981 | 0.2990 | 0.2752 | 0.2633 | 0.2346 |
| | 42 ($H_2SO_4$ 0.01 mM) | 0.3013 | 0.3120 | 0.3041 | 0.3024 | 0.2885 |
| | 43 ($H_2SO_4$ 0.02 mM) | 0.3068 | 0.3155 | 0.3009 | 0.2832 | 0.2562 |
| | 44 ($H_2SO_4$ 0.05 mM) | 0.3140 | 0.3159 | 0.2934 | 0.2660 | 0.2092 |

TABLE 9-2

|  | | Immediately after preparation | After 1 month | After 2 months | After 3 months | After 4 months |
|---|---|---|---|---|---|---|
| Comparative Example 4 | | 0.0% | −1.4% | −13.2% | −16.7% | −27.4% |
| Experimental Example | 41 ($H_2SO_4$ 0.005 mM) | 0.0% | 0.3% | −7.7% | −11.7% | −21.3% |
| | 42 ($H_2SO_4$ 0.01 mM) | 0.0% | 3.6% | 0.9% | 0.4% | −4.2% |
| | 43 ($H_2SO_4$ 0.02 mM) | 0.0% | 2.8% | −1.9% | −7.7% | −16.5% |
| | 44 ($H_2SO_4$ 0.05 mM) | 0.0% | 0.6% | −6.6% | −15.3% | −33.4% |

As apparent from Table 8-2, the reduction in absorbance of Experimental Examples 37 to 39 in which the molar concentration of sulfuric acid contained is lower than that of Nile Blue is moderate at any point of time compared to Comparative Example 3 which does not contain sulfuric acid. Thus, the storage stability of Nile Blue solutions is improved.

Further as apparent from Table 9-2, the reduction in absorbance of Experimental Examples 41 to 43 in which the molar concentration of sulfuric acid contained is lower than that of Nile Blue is moderate at any point of time compared to Comparative Example 4 which does not contain sulfuric acid. Thus, the storage stability of Nile Blue solutions is improved.

In particular, the rates of change in absorbance after 4 months of Experimental Examples 39 and 42 in which the molar concentration ratio between Nile Blue and sulfuric acid was 2:1 to 1:1 were 0.0% and −4.2%, respectively, showing particularly favorable storage stability thereof.

Thus, it is demonstrated that the storage stability of Nile Blue solutions is improved by adding an acid to the Nile Blue solutions at the concentration which is equal to or lower than the molar concentration of Nile Blue.

Incidentally, the optimum concentrations of sulfuric acid in the Nile Blue solutions were different between Experimental Examples 37 to 40 and 41 to 44. It is considered to be due to the difference in purity of Nile Blue contained in the commercial Nile Blue reagents, and may be within the range of an error.

Experimental Examples 45 to 48

Platelet Staining Property of Reagents for Measuring Platelets Containing Nile Blue and Acid The following experiments were carried out in order to study the staining property of platelets of the reagents for measuring platelets containing Nile Blue.

The reagents for measuring platelets and dilution reagent having the following compositions were prepared.

| (1) Reagents for measuring platelets | |
|---|---|
| Dye for staining platelets | At the concentrations shown in Table 10 |
| Ethylene glycol | 1 L |
| (2) Dilution solution | |
| Tricine (buffering agent) | 1.8 g |
| Lauryltrimethylammonium chloride (LTAC) | 0.15 g |
| Purified water | 1 L |
| (adjusted to pH 9.0 and osmotic pressure 200 mOsm/kg.H2O) | |

The dyes for measuring platelets used were the dyes shown in Table 10 at the concentrations shown in Table 10. The final concentrations of the dye in the mixture of the reagent, dilution solution and a sample are shown in parentheses. The chemical formulae of the dyes are shown in Table 10.

The measurements of platelets were carried out as described in Experimental Examples 9 to 13.

TABLE 10

| | Dye | Conc. | Structure | Results |
|---|---|---|---|---|
| Ex. 45 | Nile Blue A (Wako Pure Chemicals) | 18.4 ppm (0.3 ppm) | [structure with $1/2SO_4^{2-}$, $H_2N$, O, $N^+(CH_2CH_3)_2$] | Sufficient staining of platelets |
| Ex. 46 | Methylene Blue NNX (Sigma) | 102.5 ppm (2 ppm) | [structure with $H_3C$, $CH_3$, $C_2H_5HN$, $NHC_2H_5$, $S^+$, $Cl^-$] | Insufficient staining of platelets |

TABLE 10-continued

| Dye | Conc. | Structure | Results |
| --- | --- | --- | --- |
| Ex. 47 | Cresyl Violet Acetate (Sigma) | 1025 ppm (20 ppm) | No staining |
| Ex. 48 | Basic Green 5 (Tokyo Chemical Industry) | 1025 ppm (20 ppm) | Insufficient staining of platelets |

The scattergrams obtained with Experimental Examples 45 to 48 are shown in FIGS. 16 to 19, and their subsections, respectively. In each Figure, (a) is a scattergram having the y-axis of forward scattered light intensity and the x-axis of fluorescence intensity, and (b) is a scattergram in which the y-axis of the scattergram (a) is converted to the logarithms. In (b), the area where platelets appear is shown with a solid line.

The measurement results with the Experimental Examples are shown in Table 10.

Figure 16A:
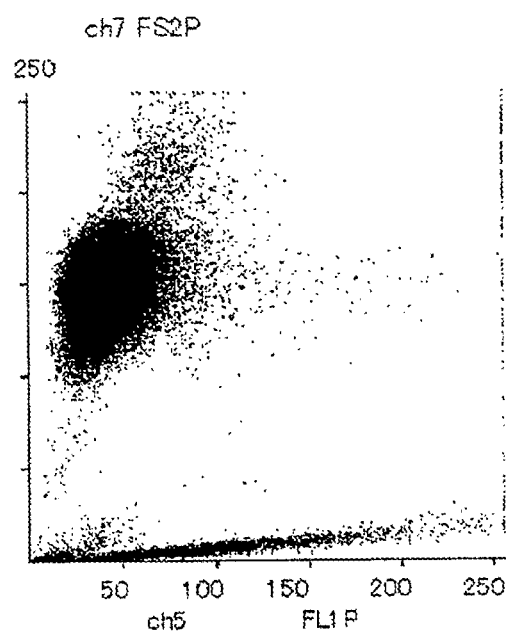
FIGS. 16A-16B show scattergrams obtained by the platelet measurement using the reagent for measuring platelets of Experimental Example 45.
Figure 16B:
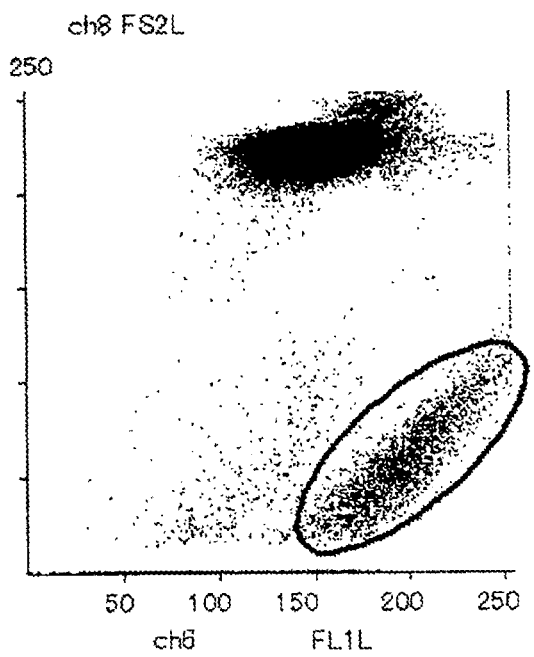
Figure 17A:
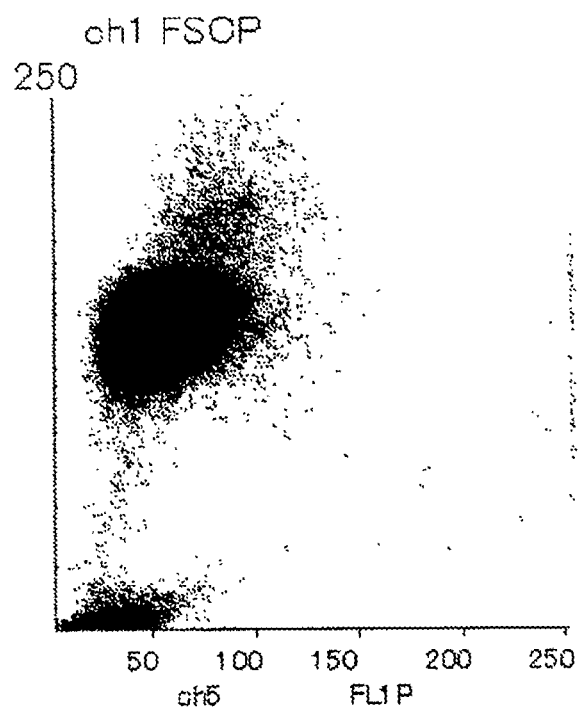
FIGS. 17A-17B show scattergrams obtained by the platelet measurement using the reagent for measuring platelets of Experimental Example 46.
Figure 17B:
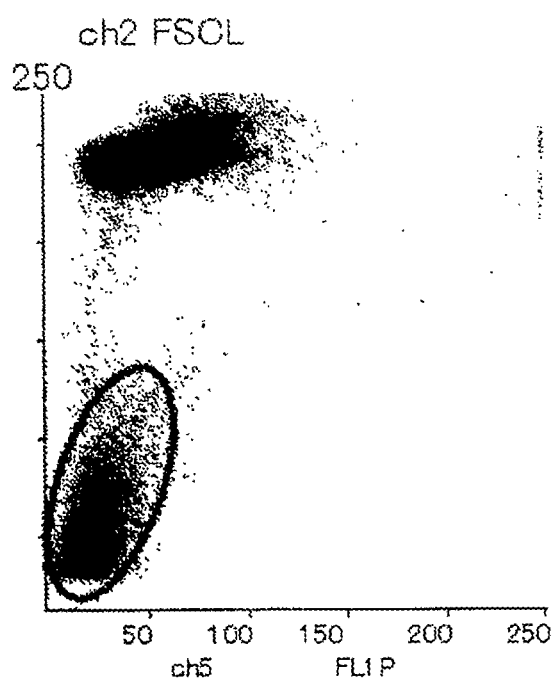
Figure 18A:
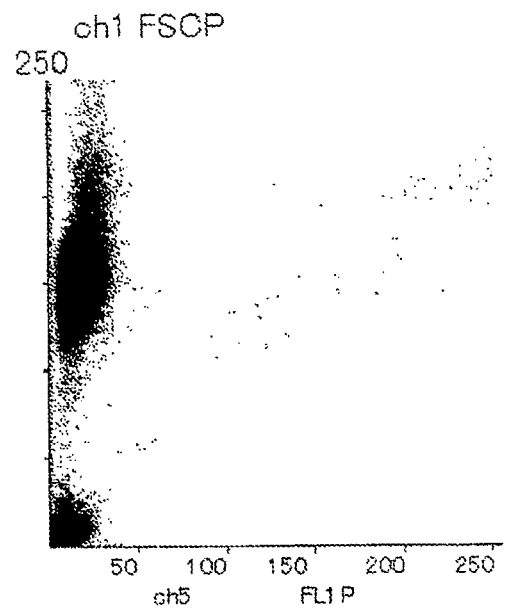
FIGS. 18A-18B show scattergrams obtained by the platelet measurement using the reagent for measuring platelets of Experimental Example 47.
Figure 18B:
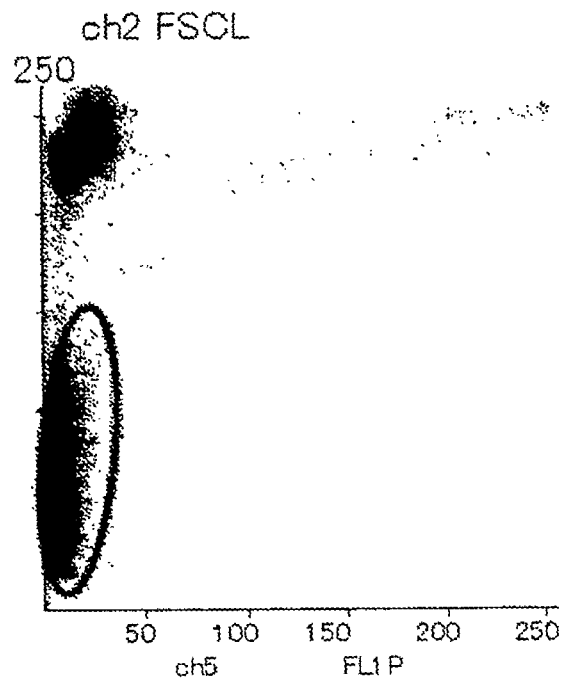
Figure 19A:
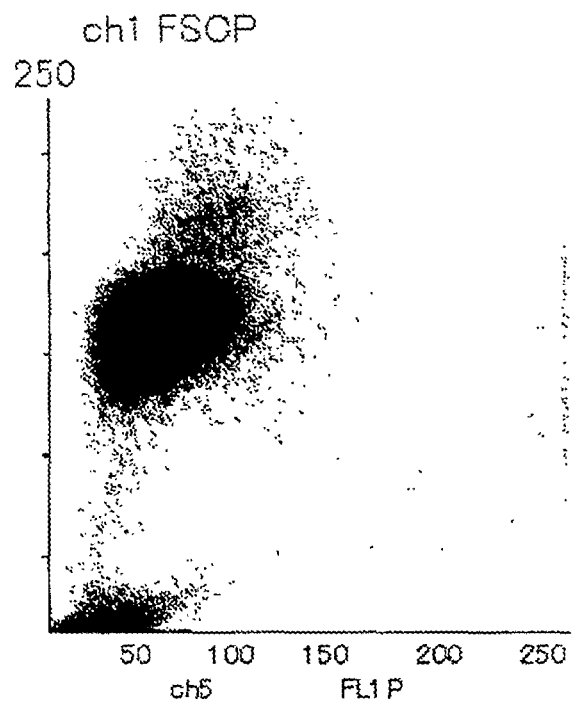
FIGS. 19A-19B show scattergrams obtained by the platelet measurement using the reagent for measuring platelets of Experimental Example 48.
Figure 19B:
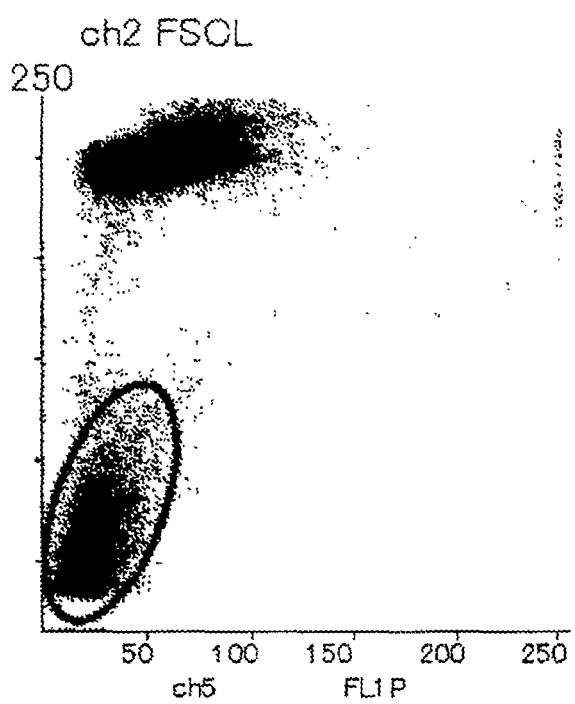

As shown in FIG. 16, and its subsections, when Experimental Example 45 was used in which Nile Blue was used as the dye, the group of platelets appears at the are having high fluorescence on the scattergram, showing that platelets were stained sufficiently.

On the other hand, when Experimental Examples 46 to 48 were used, in which the dyes other than Nile Blue were used, the group of platelets was concentrated at the area having low fluorescence on the scattergram, showing that the staining properties of platelets were not sufficient.

Thus, it is suggested that, when Nile Blue is used as the dye for measuring platelets, platelets can be sufficiently stained compared to the other dyes. Further, it is suggested that, when platelets were stained with Nile Blue, platelets can accurately be detected with forward scattered light intensity and fluorescence intensity.

Next, it was studied whether platelets could be specifically stained by using the reagent for measuring platelets of Experimental Example 45 containing Nile Blue and an acid even when blood contained the contaminants such as lipid particles, according to the similar experiments as described in Examples 9 to 13.

Figure 20A:
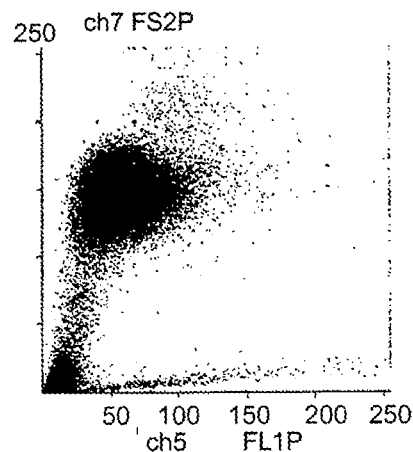
FIGS. 20A-20C show scattergrams obtained by the measurement of blood containing fragmented red cells using the reagent for measuring platelets of Experimental Example 45.
Figure 20B:
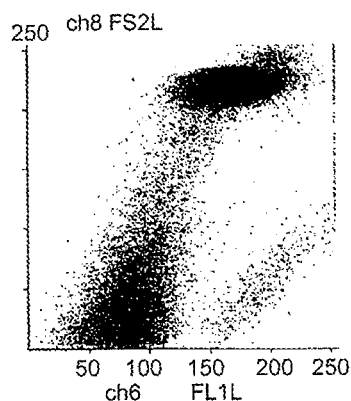
Figure 20C:
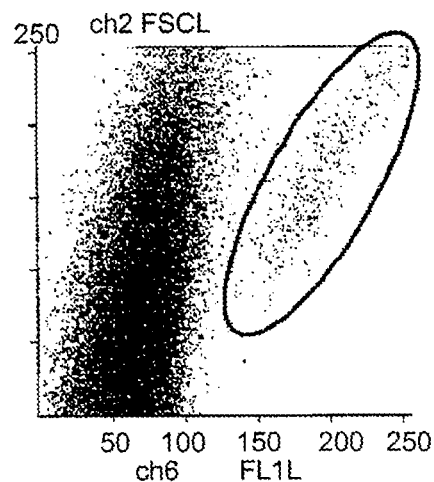
Figure 21A:
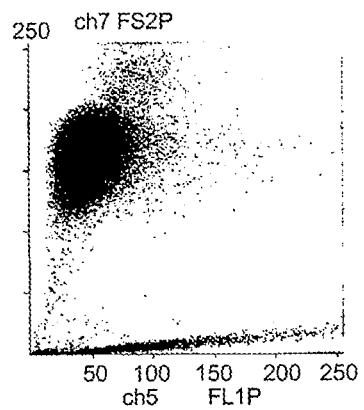
FIGS. 21A-21C show scattergrams obtained by the measurement of blood containing lipid particles using the reagent for measuring platelets of Experimental Example 45.
Figure 21B:
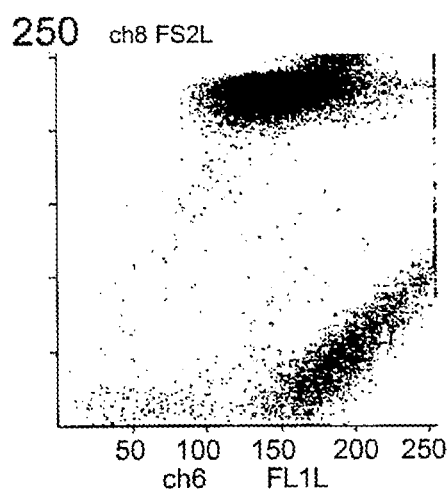
Figure 21C:
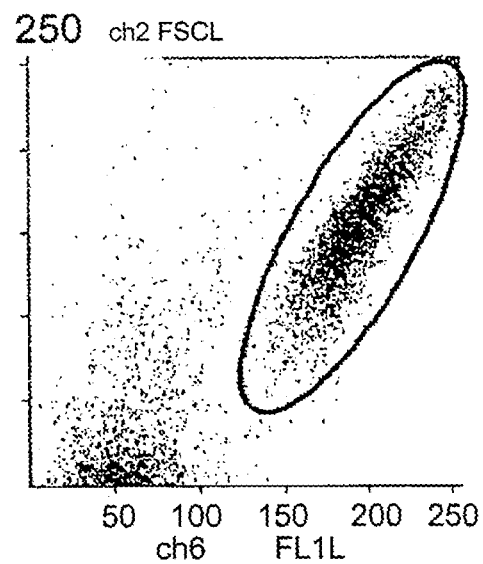

FIGS. 20 and 21, and their subsections, show the scattergrams obtained by measuring blood containing fractured red cells and blood containing lipid particles with the reagent for measuring platelets of Experimental Example 45. In each Figure, (a) is a scattergram having the y-axis of forward scattered light intensity and the x-axis of fluorescence intensity, (b) is a scattergram in which the y-axis of the scattergram (a) is converted to the logarithms, and (c) is a magnified view of the area where platelets appear in (b). In (c), the area where platelets appear is shown with a solid line.

The results in FIGS. 20 and 21, and their subsections, show that the groups of platelets contained in the samples appear on the scattergrams distinctively from other components in the samples such as fractured red cells or lipid particles. According to these results, it is demonstrated that platelets can be distinctively detected and accurately measured with the reagents for measuring platelets of the present invention even when blood contains the contaminants such as fractured red cells or lipid particles.

The present application relates to Japanese Patent Application Nos. 2008-36013, 2008-79785 and 2008-247484 respectively filed on Feb. 18, 2008, Mar. 26, 2008 and Sep. 26, 2008, whose claims, specifications, drawings and abstracts are incorporated herein by reference.

The invention claimed is:

1. A method for measuring platelets in a sample comprising the steps of:
    staining the platelets in the sample with a dye by mixing the dye and the sample to prepare a measurement sample, the dye being a compound of the following formula (III):

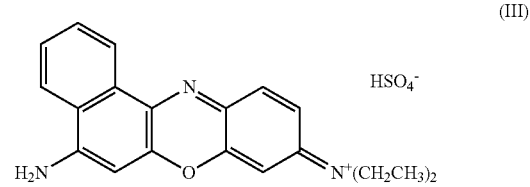

(III)

applying light to cells in the obtained measurement sample to detect scattered light and fluorescence emitted from the cells; and
detecting platelets contained in the measurement sample based on the detected scattered light and fluorescence.

2. The method according to claim 1, which further comprises a step of counting the detected platelets.

3. The method according to claim 1, which further comprises a step of accelerating the staining of platelets by the dye by mixing a staining accelerating agent and the sample.

4. The method according to claim 3, wherein the accelerating agent is a cationic surfactant.

5. The method according to claim 4, wherein the cationic surfactant is a compound of the following formula (I):

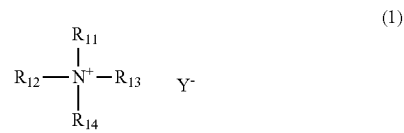

(I)

wherein $R_{11}$ is an alkyl group having 8 to 12 carbon atoms; $R_{12}$, $R_{13}$ and $R_{14}$ are the same or different from each other and are an alkyl group having 1 to 6 carbon atoms; and Y is an anion.

6. The method according to claim 1, which further comprises diluting a mixture of the sample and the dye by mixing the sample, the dye and a diluent to prepare the measurement sample.

7. The method according to claim 1, wherein the concentration of the dye in the measurement sample is 0.05 to 5 ppm.

8. The method according to claim 1, wherein the scattered light is side scattered light.

9. The method according to claim 1, wherein the wavelength of the light is 600 to 680 nm.

10. A method for measuring platelets comprising the steps of:
staining the platelets in the sample with a dye by mixing the dye, an acid and the sample to prepare a measurement sample, the dye being a compound of the following formula (II):

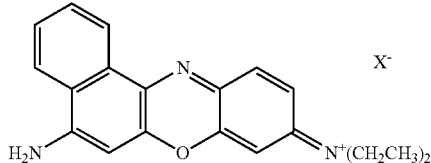

(II)

wherein X is an anion selected from the group consisting of $HSO_4^-$, ½ $SO_4^{2-}$, $Cl^-$ and $ClO_4^-$;

applying light to cells in the obtained measurement sample to detect scattered light and fluorescence emitted from the cells; and detecting platelets contained in the measurement sample based on the detected scattered light and fluorescence.

11. The method for measuring platelets according to claim 10, which further comprises a step of counting the detected platelets.

12. The method according to claim 10, which further comprises a step of accelerating the staining of platelets by the dye by mixing a staining accelerating agent and sample.

13. The method according to claim 12, wherein the accelerating agent is a cationic surfactant.

14. The method according to claim 13, wherein the cationic surfactant is a compound of the following formula (I):

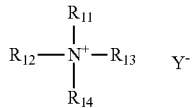

(I)

wherein $R_{11}$ is an alkyl group having 8 to 12 carbon atoms; $R_{12}$, $R_{13}$ and $R_{14}$ are the same or different from each other and are an alkyl group having 1 to 6 carbon atoms; and Y is an anion.

15. The method according to claim 10, which further comprises diluting a mixture of the sample and the dye by mixing the sample, the dye and a diluent to prepare the measurement sample.

16. The method according to claim 10, wherein the concentration of the dye in the measurement sample is 0.05 to 5 ppm.

17. The method according to claim 10, wherein the scattered light is side scattered light.

18. The method according to claim 10, wherein the acid is one selected from the group consisting of sulfuric acid, phosphoric acid, perchloric acid, hydrochloric acid, hydrofluoric acid, hydroiodic acid, hydrobromic acid, hydrocyanic acid, hydroisocyanic acid, hydrogen sulfide, and hydrogen azide.

19. The method according to claim 10, wherein the sample is mixed with a reagent comprising the dye and the acid, the ratio of molar concentration of the dye and the acid being 10:1 to 1:1.

20. A method for measuring platelets in a sample comprising the steps of:
mixing a first reagent in a first container and a sample, the first reagent comprising a dye of the following formula (III):

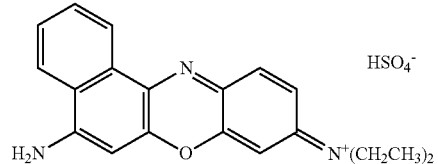

(III)

to stain the platelets by the dye;

mixing a second reagent in a second container and the mixture of the first reagent and the sample to prepare a measurement sample, the second reagent comprising a buffering agent;

applying light to cells in the obtained measurement sample to detect scattered light and fluorescence emitted from the cells; and detecting platelets contained in the measurement sample based on the detected scattered light and fluorescence.

* * * * *